US011802865B2

(12) United States Patent
Dixon et al.

(10) Patent No.: US 11,802,865 B2
(45) Date of Patent: Oct. 31, 2023

(54) UTILIZING ATREF DATA WITH CHEMOMETRIC ANALYSIS FOR DETERMINING THE TYPES OF POLYETHYLENE PRESENT IN POLYMER BLENDS AND MULTILAYER FILMS

(71) Applicant: Chevron Phillips Chemical Company LP, The Woodlands, TX (US)

(72) Inventors: JaNeille K. Dixon, Bartlesville, OK (US); Todd A. Robinson, Owasso, OK (US); James A. Solis, Owasso, OK (US); Justin W. Kamplain, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 135 days.

(21) Appl. No.: 17/562,224

(22) Filed: Dec. 27, 2021

(65) Prior Publication Data

US 2023/0204561 A1   Jun. 29, 2023

(51) Int. Cl.
*G01N 33/44* (2006.01)
*C08J 99/00* (2006.01)
(Continued)

(52) U.S. Cl.
CPC ........... *G01N 33/442* (2013.01); *C08F 10/02* (2013.01); *C08J 99/00* (2013.01); *G01N 30/14* (2013.01);
(Continued)

(58) Field of Classification Search
None
See application file for complete search history.

(56) References Cited

U.S. PATENT DOCUMENTS 3,248,179 A    4/1966  Norwood
4,501,885 A    2/1985  Sherk
(Continued)

FOREIGN PATENT DOCUMENTS

EP    1756175 B1    2/2014
JP    2011085564 A  *  4/2011   ............. G01N 24/08

OTHER PUBLICATIONS

Machine-generated translation of Detailed Description/Claims of JP 2011-085564 A. (Year: 2011).*

(Continued)

*Primary Examiner* — Fred M Teskin
(74) *Attorney, Agent, or Firm* — Conley Rose, P.C.

(57) ABSTRACT

A method of analyzing a polymer resin comprising: providing a polymer resin sample having two or more polymer components; subjecting the sample to aTREF analysis to yield aTREF elution trace by contacting the sample with aTREF solvent to form sample solution; introducing sample solution into aTREF column and allowing elution of polymer components at different elution rates along the column; eluting from the aTREF column an aTREF eluent comprising the polymer components eluting at different rates; and subjecting the aTREF eluent to IR detection to yield the aTREF elution trace; identifying the components of the sample to yield identified components by comparing the elution trace with an identification library that comprises a plurality of known polymer aTREF elution traces correlated with known polymer components characterized by identifying parameters (density, SCB, crystallization temperature, MI, HLMI, MWD); and quantifying each of the identified components to yield quantified polymer components via chemometric analysis.

20 Claims, 11 Drawing Sheets

(51) Int. Cl.
  *C08F 10/02* (2006.01)
  *G01N 30/74* (2006.01)
  *G01N 30/14* (2006.01)
(52) U.S. Cl.
  CPC .......... *G01N 30/74* (2013.01); *C08J 2323/06* (2013.01); *C08J 2323/12* (2013.01); *C08J 2323/16* (2013.01); *C08J 2325/06* (2013.01)

(56) References Cited

U.S. PATENT DOCUMENTS

| | | | |
|---|---|---|---|
| 4,588,790 | A | 5/1986 | Jenkins, III |
| 5,352,749 | A | 10/1994 | Dechellis |
| 5,436,304 | A | 7/1995 | Griffin |
| 5,565,175 | A | 10/1996 | Hottovy |
| 5,575,979 | A | 11/1996 | Hanson |
| 5,739,220 | A | 4/1998 | Shamshoum |
| 6,225,421 | B1 | 5/2001 | Promel |
| 6,239,235 | B1 | 5/2001 | Hottovy |
| 6,262,191 | B1 | 7/2001 | Hottovy |
| 6,833,415 | B2 | 12/2004 | Kendrick |
| 7,056,744 | B2 * | 6/2006 | DesLauriers ........ G01N 21/359 436/171 |
| 7,163,906 | B2 | 1/2007 | McDaniel |
| 7,619,047 | B2 | 11/2009 | Yang |
| 7,678,468 | B2 | 3/2010 | Mills |
| 7,790,820 | B2 | 9/2010 | Jensen |
| 7,960,487 | B2 | 6/2011 | Yang |
| 8,138,113 | B2 | 3/2012 | Yang |
| 8,207,280 | B2 | 6/2012 | Murray |
| 8,268,944 | B2 | 9/2012 | Yang |
| 8,323,569 | B2 | 12/2012 | Gillespie et al. |
| 8,450,436 | B2 | 5/2013 | Masino |
| 9,023,945 | B2 | 5/2015 | Mavridis |
| 9,181,372 | B2 | 11/2015 | Yang |
| 9,845,367 | B2 | 12/2017 | Ding |
| 9,850,330 | B2 | 12/2017 | Kufeld |
| 10,732,158 | B2 | 8/2020 | Kang |
| 2004/0059070 | A1 | 3/2004 | Whitte |
| 2007/0298508 | A1 | 12/2007 | DesLauriers |

OTHER PUBLICATIONS

Anja Mieth, et al., "Guidance For the Identification of Polymers in Multilayer Films Used in Food Contact Materials," JRC Technical Reports, European Union Reference Laboratory for Food Contact Materials, 2016, 70 pgs.

IUPAC Compendium of Chemical Terminology, 2nd Ed. 1997, pp. 1-1670.

Paulette Guillory, et al., "Analysis of Multi-Layer Polymer Films," Materials Today, vol. 12, No. 4, Apr. 2009, pp. 38-39.

* cited by examiner

UTILIZING ATREF DATA WITH CHEMOMETRIC ANALYSIS FOR DETERMINING THE TYPES OF POLYETHYLENE PRESENT IN POLYMER BLENDS AND MULTILAYER FILMS

TECHNICAL FIELD

The present disclosure generally relates to the analysis of polymers. More specifically, this disclosure relates to a method of determining the composition of polyethylene samples.

BACKGROUND

The versatility of polymers has made them ubiquitous in substantially everything from food packaging to airplanes, and there is a growing demand for analyzing polymer samples (e.g., polyethylene samples), as well as recycling and producing polymer articles, such as polyethylene (PE) articles, with specific properties. Analysis of polymer samples with a single polymer component can be relatively straight forward, wherein one or more conventional analysis methods can identify the resin. Multi-component polymer samples, such as multilayer polymer films, are more challenging to analyze in order to determine the composition of the polymer samples. Conventional spectroscopic techniques, such as optical microscopy, Raman spectroscopy, atomic force microscopy (AFM), infra-red (IR) spectroscopy, etc. can be used to determine the number of layers present in a sample and identify the general category of polymer (e.g., PE, polystyrene, polypropylene, etc.) in the layers. However, such conventional spectroscopic techniques cannot provide both quantitative and qualitative information about the type of polymer components, including the amounts of the different polymer components in the sample, without using several time consuming techniques for the analysis. Thus an ongoing need exists for methods of analysis of multi-component polymer samples.

BRIEF SUMMARY

Disclosed herein is a method of analyzing a polymer resin comprising (a) providing a polymer sample of the polymer resin, wherein the polymer sample comprises two or more polymer components; (b) subjecting at least a portion of the polymer sample to analytical temperature rising elution fractionation (aTREF) analysis to yield an aTREF elution trace, wherein the subjecting comprises: (i) contacting at least a portion of the polymer sample with an aTREF solvent to form a polymer sample solution; (ii) introducing at least a portion of the polymer sample solution into an aTREF column and allowing the polymer sample solution to elute along the aTREF column, wherein the two or more polymer components elute at different elution rates along the aTREF column; (iii) eluting an aTREF eluent from the aTREF column, wherein the aTREF eluent comprises the two or more polymer components eluting at the different elution rates from the aTREF column; and (iv) subjecting at least a portion of the aTREF eluent to infrared (IR) detection to yield the aTREF elution trace; (c) identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; and (d) quantifying an amount of each of the two or more identified polymer components in the polymer sample to yield two or more quantified polymer components, wherein the quantifying comprises chemometric analysis of the aTREF elution trace.

Also disclosed herein is a method of producing a polymer resin comprising (a) providing a polymer sample of the polymer resin, wherein the polymer sample comprises two or more polymer components; (b) subjecting at least a portion of the polymer sample to analytical temperature rising elution fractionation (aTREF) analysis to yield an aTREF elution trace; (c) identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; (d) quantifying an amount of each of the two or more identified polymer components in the polymer sample to yield two or more quantified polymer components, wherein the quantifying comprises chemometric analysis of the aTREF elution trace; and (e) producing the polymer resin by: (i) responsive to step (c), selecting one or more monomers that can form the two or more identified polymer components; and polymerizing the one or more monomers to produce the polymer resin; wherein the polymerizing occurs under a plurality of polymerization conditions; and wherein each polymerization condition of the plurality of polymerization conditions is selected responsive to step (d) from the group consisting of monomer concentration, comonomer concentration, hydrogen to monomer ratio, temperature, catalyst concentration, cocatalyst concentration, pressure, residence time, reactor solids concentration, and combinations thereof; (ii) responsive to step (c), selecting the two or more polymer components; and responsive to step (d), blending the two or more polymer components to produce the polymer resin; or (iii) both (i) and (ii).

Further disclosed herein is a system for analyzing a polyethylene resin comprising an analytical instrument comprising an analytical temperature rising elution fractionation (aTREF) column and an infrared (IR) detector; wherein the aTREF column is configured to receive a polyethylene sample solution, wherein the polyethylene sample solution comprises a polyethylene sample of the polyethylene resin and an aTREF solvent, wherein the polyethylene sample comprises two or more polyethylene components; wherein the aTREF column is configured to elute the two or more polyethylene components at different elution rates along the aTREF column to produce an aTREF eluent; and wherein the IR detector is configured to detect the two or more polyethylene components in the aTREF eluent and yield an aTREF elution trace; and a computer system configured to receive the aTREF elution trace from the analytical instrument, wherein the computer system comprises at least one processor; wherein the at least one processor compares the aTREF elution trace with an identification library and identifies the two or more polyethylene components of the polyethylene sample to yield two or more identified polyethylene components; wherein the identification library comprises a plurality of known polyethylene aTREF elution traces, wherein each of the plurality of known polyethylene aTREF elution traces is correlated with a known polyethylene component, wherein the known polyethylene component is characterized by an identifying parameter, and wherein the identifying parameter is selected from the group consisting of density, short chain branching, crystallization temperature, melt index, high load melt index, molecular weight distribution, and combinations thereof; and wherein the at least one processor performs chemometric analysis of the aTREF elution trace to quantify an amount of each of the two or more identified polyethylene components in the polyethylene sample to yield two or more quantified polyethylene components.

BRIEF DESCRIPTION OF THE DRAWINGS

For a detailed description of the disclosed processes and systems, reference will now be made to the accompanying drawings in which.

DETAILED DESCRIPTION

Figure 1:
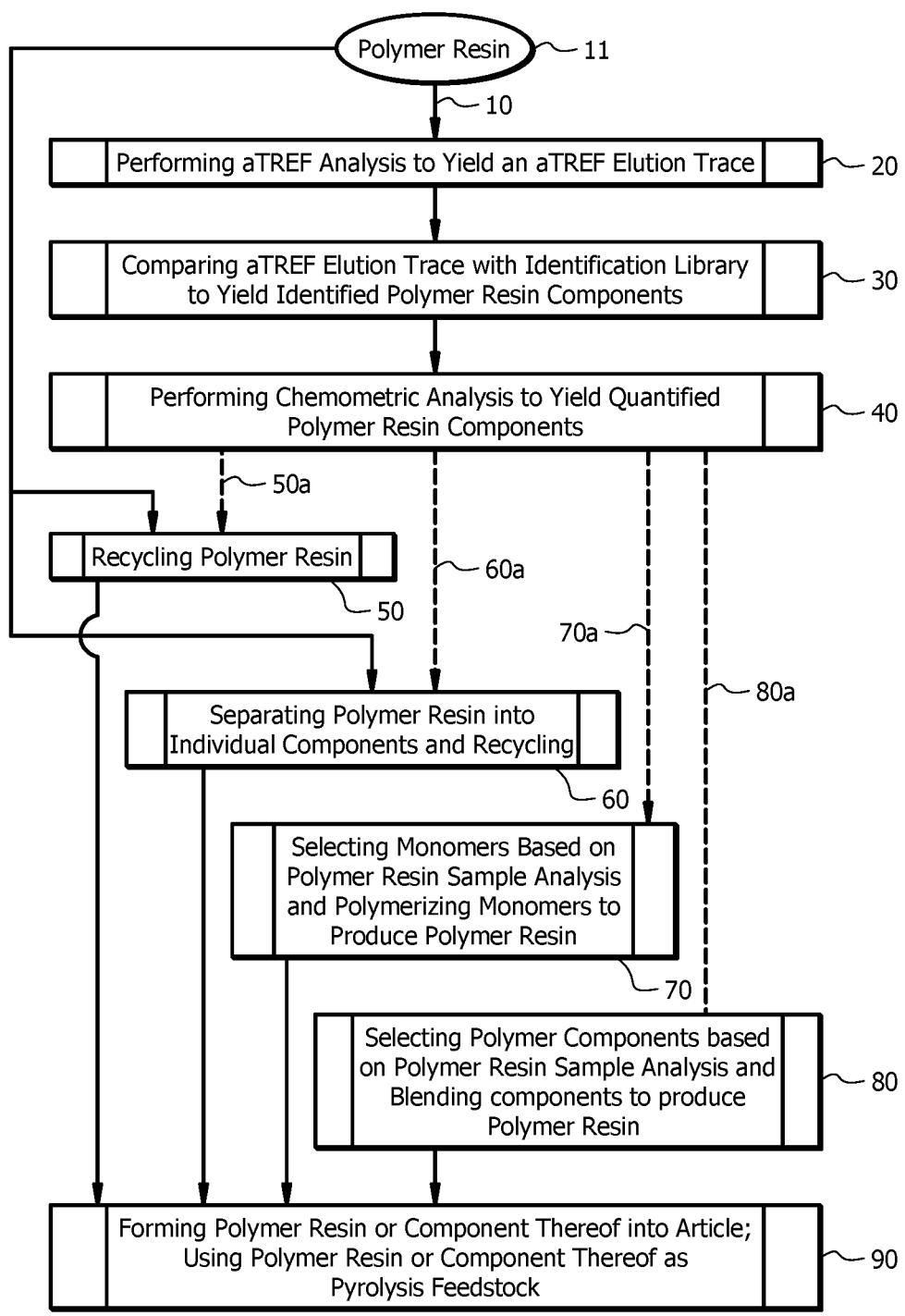
FIG. 1 illustrates a flow diagram of a process for analyzing a polymer resin.

It should be understood at the outset that although an illustrative implementation of one or more embodiments are provided below, the disclosed systems, methods, or both can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are systems, and methods of polymer analysis, for example methods of polyethylene analysis, such as methods of analyzing multi-component polyethylene samples. Also disclosed herein are systems, and processes related to petrochemical production processes, for example the production of polyethylene. The systems, and processes are generally related to the analysis, production, and optionally recycling of multi-component resins, for example multi-layer polyethylene films, bimodal polyethylene, polyethylene blends, or combinations thereof.

Analytical temperature rising elution fractionation (aTREF) data of known polyethylene (PE) samples can be used to build a library, wherein aTREF of unknown PE samples (e.g., blends of PE, mutlilayer PE films) could be compared to. Chemometric analysis of the aTREF data can help identify the general category of PE (e.g., low density polyethylene (LDPE), medium density polyethylene (MDPE), high density polyethylene (HDPE)) in the sample. Further chemometric analysis of the aTREF data can also help distinguish the type of catalyst that was used for the production of a specific type of PE, thereby further enabling the identification of the components in a PE sample (e.g., a metallocene-catalyzed resin, a Ziegler-Natta (ZN)-catalyzed resin, a chromium-catalyzed resin, a non-metallocene-catalyzed resin). Calibration curves can be established for the identified polymer sample components, thus providing for determining the amount of each polymer component in an unknown sample.

As disclosed herein, a method of analyzing a polymer resin can comprise (a) providing a polymer sample of the polymer resin, wherein the polymer sample comprises two or more polymer components; (b) subjecting at least a portion of the polymer sample to analytical temperature rising elution fractionation (aTREF) analysis to yield an aTREF elution trace, wherein the subjecting comprises: (i) contacting at least a portion of the polymer sample with an aTREF solvent to form a polymer sample solution; (ii) introducing at least a portion of the polymer sample solution into an aTREF column and allowing the polymer sample solution to elute along the aTREF column, wherein the two or more polymer components elute at different elution rates along the aTREF column; (iii) eluting an aTREF eluent from the aTREF column, wherein the aTREF eluent comprises the two or more polymer components eluting at the different elution rates from the aTREF column; and (iv) subjecting at least a portion of the aTREF eluent to infrared (IR) detection to yield the aTREF elution trace; (c) identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; and (d) quantifying an amount of each of the two or more identified polymer components in the polymer sample to yield two or more quantified polymer components, wherein the quantifying comprises chemometric analysis of the aTREF elution trace.

In some aspects, a polymer resin can be produced by (i) responsive to step (c) of identifying the two or more polymer components of the polymer sample, selecting one or more monomers that can form the two or more identified polymer components; and polymerizing the one or more monomers to produce the polymer resin; wherein the polymerizing occurs under a plurality of polymerization conditions; and wherein each polymerization condition of the plurality of polymerization conditions is selected responsive to step (d) (of quantifying an amount of each of the two or more identified polymer components in the polymer sample) from the group consisting of monomer concentration, comonomer concentration, hydrogen to monomer ratio, temperature, catalyst concentration, cocatalyst concentration, pressure, residence time, reactor solids concentration, and combinations thereof; (ii) responsive to step (c), selecting the two or more polymer components; and responsive to step (d), blending the two or more polymer components to produce the polymer resin; or (iii) both (i) and (ii).

In other aspects, at least a portion of the polymer resin having two or more quantified polymer components can be further recycled. For example, recycling of the polymer resin having two or more quantified polymer components can comprise (1) separating the two or more quantified polymer components from the polymer resin to yield two or more separated polymer components, (2) forming at least a portion of the polymer resin, at least a portion of the two or more separated polymer components, or both at least a portion of the polymer resin and at least a portion of the two or more separated polymer components into an article, (3) using at least a portion of the polymer resin, at least a portion of the two or more separated polymer components, or both at least a portion of the polymer resin and at least a portion of the two or more separated polymer components as a pyrolysis feedstock, gasification feedstock, combustion feedstock, or combinations thereof, or (4) any combination of (1)-(3).

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further, certain features of the present invention which are, for clarity, described herein in the context of separate embodiments, may also be provided in combination in a single embodiment. Conversely, various features of the invention that are, for brevity, described in the context of a single embodiment, may also be provided separately or in any sub-combination.

If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claim. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst system consisting of specific components; alternatively, consisting essentially of specific components; or alternatively, comprising the specific components and other non-recited components.

In this disclosure, while systems, processes, and methods are often described in terms of "comprising" various components, devices, or steps, the systems, processes, and methods can also "consist essentially of" or "consist of" the various components, devices, or steps, unless stated otherwise.

The term "about" as used herein means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

For purposes of the disclosure herein the term "a portion of" refers to "a fraction of," and the terms "a portion of" and "a fraction of" can be used interchangeably.

Although any methods, devices, and materials similar or equivalent to those described herein can be used in the practice or testing of the invention, the typical methods, devices, and materials are herein described.

In an aspect, a method of analyzing a polymer resin can comprise (a) providing a polymer sample of the polymer resin, wherein the polymer sample comprises two or more polymer components; and (b) subjecting at least a portion of the polymer sample to analytical temperature rising elution fractionation (aTREF) analysis to yield an aTREF elution trace. For purposes of the disclosure herein the term "providing a polymer sample" refers to supplying a polymer sample for analysis, wherein the polymer sample comprises two or more polymer components, wherein at least a portion of the provided polymer sample is subjected to aTREF analysis, and wherein the aTREF analysis can result in the identification of the polymer components in the polymer sample, as well as the quantification of the polymer components in the polymer sample. The polymer sample can be any suitable polymer sample, such as a polymer pellet sample, an article polymer sample, a film polymer sample, a pipe polymer sample, a container polymer sample, a bottle polymer sample, a drum polymer sample, an utensil polymer sample, a toy polymer sample, a membrane polymer sample, a geomembrane polymer sample, a liner polymer sample, and the like, or combinations thereof. In some aspects, the polymer resin can be a polymer film, a multi-layer polymer film, a polymer blend, a unimodal polymer, a multimodal polymer, a bimodal polymer, a trimodal polymer, a terpolymer, and the like, or combinations thereof.

While the present disclosure will be discussed in detail in the context of analyzing a polymer sample comprising two or more polymer components, it should be understood that the methods disclosed herein or any steps thereof can be applied to any suitable polymer samples, such as polymer samples comprising a single polymer component. The polymer resins that can be analyzed with the methods described herein can comprise any suitable resins compatible with the disclosed methods and materials.

aTREF analysis is an analytical technique for the analysis of semi-crystalline polymers, such as polyethylene, polypropylene, polystyrene, derivatives thereof, copolymers thereof, or combinations thereof; wherein aTREF employs column-fractionation of polymer samples in order to identify components of the polymer sample. aTREF analysis seeks to elucidate the chemical composition distribution (CCD) in a polymer sample. CCD accounts for the identity, as well as the amounts of different polymer components in a polymer sample. aTREF can be used to determine the type of polymer components present in a polymer sample, wherein the polymer components display different crystallization temperatures. For example, aTREF can be employed to distinguish between and identify whether polyethylene (PE) components in a polymer sample are high density PE (HDPE) or low density PE (LDPE), as, and without wishing to be limited by theory, more linear PEs (e.g., HDPE) tend to crystallize more readily than branched PEs (e.g., LDPE).

In an aspect, the polymer resin comprises a semi-crystalline polymer (e.g., a polymer having one or more components having the ability to form crystals), a polyethylene resin, a polypropylene resin, an ethylene-propylene copolymer, an isotactic polypropylene, a syndiotactic polypropylene, a syndiotactic polystyrene, and the like, or combinations thereof.

Generally, temperature rising elution fractionation (TREF) separates polymeric molecules based on their crystallizability. TREF separation is a two-step process in which a dissolved polymer sample is deposited (e.g., crystallized) onto a column filled with inert packing material by cooling of the column. The sample is then re-dissolved into the flowing solvent or mobile phase by raising the temperature of the column while flushing the column with solvent. The temperature at which the polymer fractions elute off the column is primarily a function of the extent of short chain branching (SCB) within the sample, and molecular weights. TREF analysis can be carried out in two different modes depending on the amount of sample to be fractionated. While a polymer sample can be analyzed using preparation TREF (pTREF), pTREF requires a relatively large amount of polymer sample in order to generate enough sample after fractionation to carry out additional characterization of polymer components. Analytical TREF (aTREF) is considered an improvement over pTREF because aTREF requires less polymer sample, as well as less solvent and less time than pTREF and the eluting polymer sample from aTREF is monitored using an on-line detector.

Typically, aTREF analysis entails placing a polymer sample into a suitable solvent (e.g., aTREF solvent) and loading it onto an aTREF column. The temperature of the aTREF column can then be lowered, wherein the polymer precipitates (e.g., crystallizes) onto the aTREF column as a function of the polymer structure (e.g., polymer branching, molecular weight). The temperature of the aTREF column can then be raised, thus causing elution of the polymer as a function of its structure. The eluted species (e.g., eluted polymer components) are then subjected to infrared (IR) detection, whereby an aTREF elution trace is produced, wherein the different polymer components in the polymer sample give rise to different peaks, and wherein the relative amounts of components in the sample provide for corresponding peak areas. While in the case of trying to distinguish between LDPE and HDPE the aTREF analysis may be relatively straight forward, when analyzing a polymer sample that contains different types of LDPE that are distinguished based on the type of catalyst that was used to produce, the analysis of the aTREF data is significantly more complex, as disclosed herein.

In an aspect, the two or more polymer components in the polymer sample comprise a metallocene-catalyzed resin, a Ziegler-Natta (ZN)-catalyzed resin, a chromium-catalyzed resin, a non-metallocene single-site-catalyzed resin (e.g., post-metallocene resin), a crosslinked resin (e.g., a resin treated with a crosslinking agent, such as a peroxide), a peroxide-treated resin, low density polyethylene (LDPE), linear low density polyethylene (LLDPE), metallocene-catalyzed linear low density polyethylene (mLLDPE), peroxide-treated linear low density polyethylene (pLLDPE), peroxide-treated metallocene-catalyzed linear low density polyethylene (pmLLDPE), ZN-catalyzed LLDPE, chromium-catalyzed LLDPE, non-metallocene single-site-catalyzed LLDPE, medium density polyethylene (MDPE), metallocene-catalyzed medium density polyethylene (mMDPE), high density polyethylene (HDPE), a plastomer, an elastomer, and the like, or combinations thereof.

In an aspect, subjecting at least a portion of the polymer sample to aTREF analysis to yield an aTREF elution trace comprises a step of contacting at least a portion of the polymer sample with an aTREF solvent to form a polymer sample solution. The polymer sample may be introduced to an analytical instrument (e.g., aTREF instrument, a crystallization elution fractionation (CEF) instrument, a crystallization analysis fractionation (CRYSTAF)-aTREF instrument, an aTREF-gel permeation chromatography (GPC) instrument), wherein the contacting of the polymer sample with the aTREF solvent is automated and performed by the analytical instrument. Alternatively, the polymer sample may be contacted with the aTREF solvent to form a polymer sample solution manually (e.g., by an operator), wherein the operator introduces the polymer sample solution to the analytical instrument. The aTREF solvent comprises a halogenated aromatic hydrocarbon solvent, 1,2,4-trichlorobenzene (TCB), ortho-dichlorobenzene (o-DCB), or combinations thereof.

In an aspect, subjecting at least a portion of the polymer sample to aTREF analysis to yield an aTREF elution trace comprises a step of introducing at least a portion of the polymer sample solution into an aTREF column and allowing the polymer sample solution to elute along the aTREF column, wherein the two or more polymer components elute at different elution rates along the aTREF column. In such aspect, at least a portion of the polymer in the polymer sample solution crystallizes out of the solution onto the aTREF column under substantially static conditions (e.g., substantially no flow of solvent through the column) to yield a column-crystallized polymer. As described herein, different polymer components in the polymer sample will crystallize at the different rates onto the aTREF column, thus providing for the ability of the aTREF to resolve the different polymer components (e.g., identify and quantify the different polymer components). Further, at least a portion of the column-crystallized polymer re-dissolves back into solution under flow conditions and elutes off the aTREF column with increasing temperature in the aTREF column. As described herein, different polymer components will solubilize at the different rates off the aTREF column, thus providing for the ability of the aTREF to resolve the different polymer components. As will be appreciated by one of skill in the art, and with the help of this disclosure, not all polymer components will yield completely resolved or distinct peaks on an aTREF elution trace, as some of the peaks for individual polymer components may overlap with each other, based on how different the individual polymer components are from each other. The chemometric analysis of the aTREF elution trace as disclosed herein can be a powerful tool in identifying resin polymer components that overlap with each other to some extent.

An example of an aTREF temperature profile ramp and elution rate is presented in the Examples below. However, and as will be appreciated by one of skill in the art, and with the help of this disclosure, different temperature ramps and elution rates are possible, wherein certain combinations of temperature ramps and elution rates will give better separation of polymer components.

In an aspect, subjecting at least a portion of the polymer sample to aTREF analysis to yield an aTREF elution trace comprises a step of eluting an aTREF eluent from the aTREF column, wherein the aTREF eluent comprises the two or more polymer components eluting at the different elution rates from the aTREF column. As described herein, polymer components with different structures will elute at different rates from the aTREF column. At least a portion of the aTREF eluent is subjected to IR detection to yield the aTREF elution trace, wherein the aTREF elution trace comprises two or more peaks that may or may not partially overlap (depending on the identity of the polymer components), wherein the two or more peaks correspond to the two or more polymer components in the polymer sample. In a typical aTREF configuration, substantially all of the aTREF eluent is subjected to IR detection. However, other aTREF configurations may be possible where not all of the aTREF eluent is subjected to IR detection.

In an aspect, the aTREF analysis can be performed on an analytical instrument selected from the group consisting of an aTREF instrument, a CEF instrument, a CRYSTAF-aTREF instrument, and combinations thereof; wherein the analytical instrument comprises the aTREF column. The analytical instrument comprising the aTREF column can be used for elucidating the CCD of a polymer sample as disclosed herein. The CEF instrument combines CRYSTAF and aTREF for elucidating the CCD of a polymer sample, and may further include the capability of performing thermal gradient interaction chromatography (TGIC) techniques. The CCD of a polymer sample can be resolved on a CRYSTAF-aTREF instrument other than a CEF instrument; wherein the CRYSTAF-aTREF instrument ma be an analytical instrument lacking TGIC. In some aspects, the CEF instrument can further comprise a capillary viscometer detector configured to provide data on composition-molar mass interdependence of the two or more polymer components in the polymer sample. Generally, the CEF instrument comes with an IR detector and has the option of adding a viscometer detector. The CEF instrument can be used in a similar manner to an aTREF instrument, however, CEF can allow for a small but substantially constant flow during the crystallization step, thereby providing for additional separation of polymer components. In some aspects, CEF can be run in aTREF mode.

In some aspects, the method of analyzing a polymer resin can further comprise using a supplemental analytical technique to additionally characterize the polymer resin, wherein the supplemental analytical technique comprises crystallization analysis fractionation (CRYSTAF), optical microscopy, atomic force microscopy (AFM), IR spectroscopy, Raman spectroscopy, inductively coupled plasma (ICP) analysis, TGIC, thermomechanical analysis (TMA), differential scanning calorimetry (DSC), nuclear magnetic resonance (NMR) spectroscopy, gel permeation chromatography (GPC), or combinations thereof. In an aspect, the method of analyzing a polymer resin can comprise using aTREF-GPC, which is also referred to as cross fractionation chromatography (CFC).

In an aspect, a method of analyzing a polymer resin can comprise a step of identifying the two or more polymer components of the polymer sample to yield two or more identified polymer components. For purposes of the disclosure herein, the term "identified polymer component" refers to the polymer component being labelled with a corresponding polymer type name (e.g., LDPE, LLDPE, MDPE, etc.) and does not imply that the polymer component has been isolated or separated out of the polymer resin via aTREF.

In an aspect, identifying the two or more polymer components of the polymer sample to yield two or more identified polymer components comprises comparing the aTREF elution trace with an identification library that comprises a plurality of known polymer aTREF elution traces, wherein each of the plurality of known polymer aTREF elution traces is correlated with a known polymer component, and wherein the known polymer component is characterized by an identifying parameter. The identifying parameter can be selected from the group consisting of density, short chain branching (SCB), crystallization temperature, melt index, high load melt index, molecular weight distribution, and combinations thereof. The identifying parameter may establish the difference between two or more polymer components in a polymer sample. For example, a polymer sample may contain two or more polymer components that differ from each other based on their individual crystallization temperature. As another example, a polymer sample may contain two or more polymer components that differ from each other based on their individual SCB values.

Density of a polymer resin or component thereof can be expressed in g/cc, and can be determined in accordance with ASTM D1505.

SCB is known for its effects on polymer properties such as stiffness, tensile properties, heat resistance, hardness, permeation resistance, shrinkage, creep resistance, transparency, stress crack resistance, flexibility, impact strength, and the solid state properties of semi-crystalline polymers such as polyethylene. For purposes of the disclosure herein, SCB can be defined as comprising chains that have a number of carbon atoms ranging from about 1 carbon atom to about 18 carbon atoms, alternatively from about 3 carbon atoms to about 10 carbon atoms, or alternatively from about 4 carbon atoms to about 6 carbon atoms. SCB content can be expressed as the number of short chain branches per 1,000 carbon atoms (SCB/1,000 carbons).

Generally, the crystallization temperature (also known as melt crystallization temperature or Tmc) of a polymer resin or component thereof refers to the temperature at which the resin or component thereof transitions to a crystalline state, and it can be measured by differential scanning calorimetry according to ASTM D3418-12.

Melt index (MI) of a polymer resin or component thereof represents the rate of flow of a molten resin or component thereof through an orifice of 0.0825 inch diameter when subjected to a force of 2.16 kg at 190° C. as determined in accordance with ASTM D1238.

High load melt index (HLMI) of a polymer resin or component thereof represents the rate of flow of a molten resin or component thereof through an orifice of 0.0825 inch diameter when subjected to a force of 21.6 kg at 190° C. as determined in accordance with ASTM D1238.

The weight average molecular weight ($M_w$) of a polymer resin or component thereof describes the size average (e.g., molecular weight distribution) of a composition and can be calculated according to equation (1):

$$M_w = \frac{\sum_i N_i M_i^2}{\sum_i N_i M_i} \quad (1)$$

wherein $N_i$ is the number of molecules of molecular weight $M_i$. All molecular weight averages are expressed in gram per mole (g/mol) or Daltons (Da), or in kg/mol or kDa. As will be appreciated by one of skill in the art, and with the help of this disclosure, the polymer resin or component thereof (e.g., polyethylene resin or component thereof) can have any suitable $M_w$, as polymer production systems can produce a wide variety of polymer resins, which can display a wide variety of $M_w$. The number average molecular weight is the common average of the molecular weights of the individual polymers and can be calculated by measuring the molecular weight $M_i$ of $N_i$ polymer molecules, summing the weights, and dividing by the total number of polymer molecules, according to equation (2):

$$M_n = \frac{\sum_i N_i M_i}{\sum_i N_i} \quad (2)$$

wherein $N_i$ is the number of molecules of molecular weight $M_i$.

The molecular weight distribution (MWD) of a polymer resin or component thereof can be calculated as the ratio of the $M_w$ to the $M_n$ ($M_w/M_n$), which can also be referred to as the polydispersity index (PDI) or more simply as polydispersity.

The identification library comprises a plurality of known polymer aTREF elution traces, wherein each known polymer aTREF elution trace has been obtained for a single know polymer resin or component thereof. The identification library functions as a "calibration data" (e.g., identification calibration data set), which refers to known data. The aTREF elution trace functions as "validation data" (e.g., identification validation data set), which is a set of data to be compared with the calibration data (e.g., identification library) in order to establish the identity of the two or more polymer components, thereby validating the identified polymer components. As will be appreciated by one of skill in the art, and with the help of this disclosure, while sometimes the aTREF elution traces will comprise completely resolved peaks (in relatively rare cases), it is more often that the peaks corresponding to the various components present in the polymer resin overlap with each other, thus rendering the identification of the individual polymer components in the polymer sample more difficult. Further, the relative amounts of individual polymer components in the polymer sample contribute to the shape (e.g., height) of the peaks, thus rendering the identification of the individual polymer components in the polymer sample difficult. Chemometric analysis (e.g., identification chemometric analysis) can be applied to the identification validation data set in order to establish the correspondence within the identification calibration data set, thereby yielding the two or more identified polymer components.

In some aspects, the identification chemometric analysis can account for the type of catalyst used for producing the two or more polymer components. For example, in aspects where the two or more polymer components comprise Ziegler-Natta-catalyzed linear low density polyethylene (ZN-LLDPE) and metallocene-catalyzed linear low density polyethylene (mLLDPE), the identification chemometric analysis can distinguish between and identify the presence of each ZN-LLDPE and mLLDPE in the same polymer sample. In an aspect, the identification chemometric analysis comprises multivariate analysis. The identification chemometric analysis can comprise principal components analysis (PCA), partial least squares (PLS) regression analysis, or both PCA and PLS regression analysis.

In an aspect, a method of analyzing a polymer resin can comprise a step of quantifying an amount of each of the two or more identified polymer components in the polymer sample to yield two or more quantified polymer components. For purposes of the disclosure herein, the term "quantified polymer component" refers to the polymer component being associated with a corresponding numerical amount value and does not imply that the polymer component has been isolated or separated out of the polymer resin via aTREF.

In an aspect, quantifying an amount of each of the two or more identified polymer components in the polymer sample to yield two or more quantified polymer components comprises chemometric analysis (e.g., quantification chemometric analysis) of the aTREF elution trace. The chemometric analysis comprises pre-processing the aTREF elution trace to yield a pre-processed aTREF elution trace, wherein the pre-processing comprises baseline correction, mean centering (MC), normalization (N), baseline correction and MC, normalization and MC, or combinations thereof. Pre-processing the aTREF elution trace provides for increased accuracy of determining the actual amount of a polymer component in the polymer sample. In other words, the pre-processing of the aTREF elution trace removes "noise" that may interfere with the accurate determination of the amount of a polymer component in the polymer sample. As will be appreciated by one of skill in the art, and with the help of this disclosure, any suitable pre-processing of the aTREF elution trace may be used.

The pre-processed aTREF elution trace can be subjected to multivariate analysis to predict the amount of each of the two or more polymer components in the polymer sample. For example, the pre-processed aTREF elution trace can be subjected to PCA followed by PLS regression analysis to predict the amount of each of the two or more polymer components in the polymer sample, thereby quantifying the amount of each of the two or more identified polymer components in the polymer sample. The PCA of the pre-processed aTREF elution trace can further comprise root mean square (RMS) analysis to determine a number of principal components (PCs) necessary to predict the amount of each of the two or more polymer components in the polymer sample; and wherein the number of PCs is an integer equal to or greater than 1, alternatively equal to or greater than 2, alternatively equal to or greater than 3, alternatively equal to or greater than 4, alternatively equal to or greater than 5, or alternatively equal to or greater than 6. In some aspects, the number of PCs is 1. In other aspects, the number of PCs is 2. In yet other aspects, the number of PCs is 3. In still yet other aspects, the number of PCs is 4. In an aspect, the RMS analysis comprises root mean square error of cross validation (RMSECV) analysis.

In an aspect, the quantification chemometric analysis can further comprise employing a calibration set (e.g., quantification calibration set, quantification calibration data set) that comprises calibration data (e.g., quantification calibration data) for known polymer resins having a known amount of each of the two or more identified polymer components. The quantification calibration data set can be part of a quantification library. The quantification library may comprise a plurality of known polymer aTREF elution traces, wherein each known polymer aTREF elution trace has been obtained for known polymer resins having a known amount of each of the two or more identified polymer components. The quantification library may function as the quantification calibration data set. The pre-processed aTREF elution trace functions as the quantification validation data set, which is compared with the quantification calibration data set (e.g., quantification library) in order to establish the amounts of the two or more polymer components in the polymer sample, thereby validating the quantified polymer components.

In an aspect, a method of producing a polymer resin can comprise analyzing a polymer resin as disclosed herein to yield identified polymer components and quantified polymer components.

In some aspects, subsequent to identifying the polymer components present in the polymer sample as disclosed herein, a method of producing a polymer resin can comprise selecting the two or more polymer components based on the identified polymer components, and blending the two or more selected polymer components to produce the polymer resin. In an aspect, the polymer resin can be produced by blending the two or more selected polymer components, for example in a mixer, blender, extruder, single screw extruder, twin screw extruder, and the like, or combinations thereof.

In other aspects, subsequent to identifying the polymer components present in the polymer sample as disclosed herein, a method of producing a polymer resin or component thereof can comprise selecting one or more monomers that can form the two or more identified polymer components and polymerizing the one or more selected monomers to produce the polymer resin or component thereof. The polymerizing can occur under a plurality of polymerization conditions, as described in more detail later herein; wherein each polymerization condition of the plurality of polymerization conditions is selected based on the quantified polymer components (e.g., based on the amounts of identified polymer components necessary to form the polymer resin) from the group consisting of monomer concentration, comonomer concentration, hydrogen to monomer ratio, temperature, catalyst concentration, cocatalyst concentration, pressure, residence time, reactor solids concentration, and combinations thereof.

In yet other aspects, subsequent to identifying the polymer components present in the polymer sample as disclosed herein, a method of producing a polymer resin or component thereof can comprise selecting one or more monomers that can form the two or more identified polymer components and polymerizing the one or more selected monomers to produce one or more polymer components, wherein the produced polymer components may be subsequently blended with each other and/or selected polymer components to produce the polymer resin. In such aspects, the polymer components can be blended to produce the polymer resin, for example in a mixer, blender, extruder, single screw extruder, twin screw extruder, and the like, or combinations thereof.

In an aspect, polymerizing an olefin (e.g., polymerizing ethylene) can comprise contacting an olefin monomer (e.g., ethylene), such as the selected one or more monomers, with a catalyst system within a reaction zone (e.g., polymerization reaction zone) or reactor to form a polyolefin (e.g., polyethylene), such as the polymer resin or component thereof. Catalyst systems can include any suitable catalyst system(s) (e.g., catalyst, co-catalyst, support, activator) useful for polymerizing olefin monomers, such as chromium based catalyst systems, single site transition metal catalyst systems (including metallocene catalyst systems), Ziegler-Natta catalyst systems, non-metallocene single-site catalyst systems (e.g., post-metallocene catalysts), and the like, or combinations thereof. As will be appreciated by one of skill in the art, and with the help of this disclosure, catalysts may be activated for subsequent polymerization and may or may not be associated with a support material, for example. Further, and as will be appreciated by one of skill in the art, and with the help of this disclosure, polymerization conditions (e.g., equipment, process conditions, reactants, additives and any other materials used in polymerization processes) will vary in a given process, depending on the desired composition and properties of the polymer being formed. Furthermore, and as will be appreciated by one of skill in the art, and with the help of this disclosure, each reactor can have 1, 2, 3, 4, 5, or more reaction zones.

For purposes of the disclosure herein, the term "polymerization reactor" can include any reactor capable of polymerizing olefin monomers (e.g., ethylene) and optionally comonomers (one or more than one comonomers) to produce polyolefin polymers (polyolefins), such as homopolymers, copolymers, terpolymers, and the like. Polyolefins produced in the polymerization reactor can be referred to as resins or polymers. Nonlimiting examples of reactors suitable for use in the present disclosure include a loop slurry reactor, a fluidized bed gas phase reactor, a solution reactor, a continuous stirred-tank reactor (CSTR), an autoclave, a tubular reactor, a multi-zone circulating reactor (MZCR), and the like, or combinations thereof.

The polymerization reactor can comprise one or more reaction zones (e.g., polymerization reaction zones), wherein each of the reaction zones can be individually characterized by process operating parameters, such as reactant concentrations (e.g., monomer concentration, comonomer concentration, hydrogen concentration), catalyst system concentration (e.g., catalyst concentration, cocatalyst concentration), temperature, pressure, residence time, reactor solids concentration, and the like. The desired polymerization conditions in one of the reaction zones can be the same as or different from the operating conditions of any other reaction zones involved in the overall process of producing the polymers of the present disclosure.

The various types of reactors include those that can be referred to as a batch reactor, slurry reactor, gas-phase reactor, solution reactor, high pressure reactor, tubular reactor, autoclave reactor, and the like, or combinations thereof. Suitable process conditions (e.g., polymerization conditions) are used for the various reactor types. Gas phase reactors can comprise fluidized bed reactors or staged horizontal reactors. Slurry reactors can comprise vertical or horizontal loops. High pressure reactors can comprise autoclave or tubular reactors. Reactor types can include batch or continuous processes. Continuous processes can use intermittent or continuous product discharge or transfer. Processes can also include partial or full direct recycle of unreacted monomer, unreacted comonomer, catalyst, co-catalyst, diluents, or combinations thereof.

In an aspect, polymerization reactor systems suitable for use in the present disclosure can comprise one type of reactor in a system or multiple reactors of the same or different type (e.g., a single reactor, dual reactor, more than two reactors), operated in any suitable configuration. Production of polymers in multiple reactors can include several stages in at least two separate polymerization reactors interconnected by a transfer system making it possible to transfer the polymers resulting from a first polymerization reactor into a second reactor. The desired polymerization conditions in one of the reactors can be the same as or different from the operating conditions of any other reactors involved in the overall process of producing the polymers of the present disclosure. Alternatively, polymerization in multiple reactors can include the transfer, either manual or automatic, of polymer from one reactor to subsequent reactor or reactors for additional polymerization.

Multiple reactor systems can include any combination including, but not limited to, multiple loop reactors, multiple gas phase reactors, a combination of loop and gas phase reactors, multiple high pressure reactors, or a combination of high pressure with loop reactors, gas phase reactors, or both loop and gas phase reactors. The multiple reactors can be operated in series, in parallel, or both in series and in parallel.

In an aspect, polymerizing ethylene as disclosed herein can comprise polymerizing ethylene in polymerization reactor systems comprising a single reactor, comprising two reactors, and comprising more than two reactors. The polymerization reactor system can comprise a slurry reactor, a gas-phase reactor, a solution reactor, as well as multi-reactor combinations thereof. In an aspect, any suitable reactor configuration can be employed to produce the polymer of the present disclosure.

In an aspect, a polymerization reactor system can comprise a fast fluidization reaction zone, a plug flow reaction zone, or both a fast fluidization reaction zone and a plug flow reaction zone. In such aspect, a first reaction zone (e.g., a riser) can comprise a fast fluidization reaction zone, wherein fast fluidization conditions can be established by feeding a gas mixture comprising one or more olefins (e.g., ethylene and comonomer) at a velocity higher than a transport velocity of polymer particles. Generally, fast fluidization conditions refer to a velocity of a gas mixture of from about 0.5 meters per second (m/s) to about 15 m/s, or alternatively from about 0.8 m/s to about 5 m/s. In such aspect, a second reaction zone (e.g., downcomer) can comprise a plug flow reaction zone, wherein polymer particles can flow under the action of gravity in a more dense form (e.g., mass of polymer per volume of reactor is greater in the downcomer than in the riser), such that high values of density of the solid polymer particles are reached (e.g., mass of polymer per volume of reactor). Such high density values can approach the bulk density of the produced polymer. The polymer can flow vertically down through the downcomer in a "plug flow" (e.g., packed flow mode), such that only small quantities of gas are entrained between the polymer particles. Generally, a plug flow reactor or reaction zone (PFR), also known as a flow tube reactor or reaction zone, comprises a fluid flowing through the reactor or reaction zone as a series of infinitely thin coherent "plugs," each plug having a uniform composition, traveling in the axial direction of the flow tube reactor or reaction zone. In PFRs, it is assumed that as a plug flows through the reactor or reaction zone, the fluid is perfectly mixed in the radial direction, but not in the axial direction (forwards or backwards). In some aspects, a single reactor can comprise both the fast fluidization reaction zone and the plug flow reaction zone. In other aspects, a first reactor can comprise the fast fluidization reaction zone, and a second reactor can comprise the plug flow reaction zone. Fast fluidization reaction zones and plug flow reaction zones are described in more detail in U.S. Pat. No. 9,023,945; which is incorporated by reference herein in its entirety.

According to one aspect of this disclosure, the polymerization reactor system can comprise at least one loop slurry reactor comprising vertical or horizontal loops. Monomer, diluent, catalyst, and optionally any comonomer can be continuously fed to a loop reactor where polymerization occurs. Generally, continuous processes can comprise the continuous introduction of a monomer, an optional comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer, comonomer, or combinations thereof. Various technologies can be used for this separation step including but not limited to, flashing that can include any combination of heat addition and pressure reduction; separation by cyclonic action in either a cyclone or hydrocyclone; or separation by centrifugation.

A suitable slurry polymerization process (also known as the particle form process), is disclosed, for example, in U.S. Pat. Nos. 3,248,179; 4,501,885; 5,565,175; 5,575,979; 6,239,235; 6,262,191; and 6,833,415; each of which is incorporated by reference herein in its entirety.

Suitable diluents used in slurry polymerization include, but are not limited to, the monomer, and optionally, the comonomer, being polymerized and hydrocarbons that are liquids under polymerization reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used.

According to another aspect of this disclosure, the polymerization reactor system can comprise at least one gas phase reactor. Such polymerization reactor systems can employ a continuous recycle stream containing one or more monomers continuously cycled through a fluidized bed in the presence of a catalyst under polymerization conditions. A recycle stream can be withdrawn from the fluidized bed and recycled back into the reactor. Simultaneously, a polymer product can be withdrawn from the reactor and new or fresh monomer can be added to replace the polymerized monomer. Likewise, copolymer product can optionally be withdrawn from the reactor and new or fresh comonomer can be added to replace polymerized comonomer, polymerized monomer, or combinations thereof. Such gas phase reactors can comprise a process for multi-step gas phase polymerization of olefins, in which olefins are polymerized in the gaseous phase in at least two independent gas phase polymerization zones (e.g., reaction zones) while feeding a catalyst-containing polymer formed in a first polymerization zone to a second polymerization zone. Gas phase reactors are disclosed in U.S. Pat. Nos. 5,352,749; 4,588,790; and 5,436,304; each of which is incorporated by reference herein in its entirety.

According to yet another aspect of this disclosure, a high-pressure polymerization reactor can comprise a tubular reactor or an autoclave reactor. Tubular reactors, autoclave reactors, or both can have several zones where fresh monomer (optionally, comonomer), or a polymerization catalyst system can be added. Monomer (optionally, comonomer) can be entrained in an inert dense fluid stream (well above the critical point at such high pressures) and introduced into the reactor (typically introduced in multiple locations on the reactor). Polymerization catalyst system components can be entrained in a monomer feed stream, introduced as liquids or supercritical fluids directly into the reactor, or both. The fluid streams can be intermixed in the reactor to initiate and sustain polymerization. Heat and pressure can be employed appropriately to obtain optimal polymerization reaction conditions.

According to still yet another aspect of this disclosure, the polymerization reactor system can comprise a solution polymerization reactor wherein the monomer (optionally, comonomer) can be contacted with a catalyst composition by suitable stirring or other means. A carrier comprising an inert organic diluent or excess monomer (optionally, comonomer) can be employed. If desired, the monomer, optional comonomer, or both can be brought in the vapor phase into contact with a catalytic reaction product, in the presence or absence of liquid material. A polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactor systems suitable for the disclosed systems and processes can further comprise any combination of at least one raw material feed system, at least one feed system for catalyst or catalyst components, and at least one polymer recovery system. Suitable reactor systems can further comprise systems for feedstock purification, catalyst storage and preparation, extrusion, reactor cooling, polymer recovery, fractionation, recycle, storage, loadout, laboratory analysis, and process control.

Conditions (e.g., polymerization conditions) that are controlled for polymerization efficiency and to provide desired resin properties include temperature; pressure; type of catalyst or co-catalyst, quantity of catalyst or co-catalyst, or both; concentrations of various reactants; partial pressures of various reactants; reactor solids concentration; reactor residence time (e.g., reaction zone residence time); or combinations thereof. Various polymerization conditions can be held substantially constant, for example, for the production of a particular polymer resin, such as a polymer resin or component thereof having a specific composition (e.g., the composition of the analyzed polymer sample, as described by the identified and quantified polymer components). The polymerization conditions can be modified as necessary such that the desired polymer resin or component thereof having a specific composition (e.g., the composition of the analyzed polymer sample, as described by the identified and quantified polymer components) is produced.

Polymerization temperature can affect catalyst productivity, polymer molecular weight and molecular weight distribution. Suitable polymerization temperature can be any temperature below the de-polymerization temperature according to the Gibbs Free energy equation. The polymerization temperature can have as upper limit a temperature at which the monomer (e.g., ethylene) begins to decompose. As will be appreciated by one of skill in the art, and with the help of this disclosure, monomer decomposition temperatures are pressure dependent. Polymerization temperatures can be from about 60° C. to about 350° C., alternatively from about 60° C. to about 280° C., or alternatively from about 60° C. to about 120° C., depending upon the type of polymerization reactor. In some aspects, polymerization temperatures can be from about 70° C. to about 100° C., or alternatively from about 75° C. to about 95° C.

Suitable pressures will also vary according to the reactor and polymerization type. The pressure for liquid phase polymerizations in a loop reactor is typically less than about 1,000 psig (6.9 MPag). Pressure for gas phase polymerization is usually at about 200 psig (1.4 MPag) to about 700 psig (4.8 MPag), or alternatively at about 200 psig (1.4 MPag) to about 500 psig (3.4 MPag). High-pressure polymerization in tubular or autoclave reactors is generally run at about 20,000 psig (138 MPag) to about 75,000 psig (517 MPag). Polymerization reactors can also be operated in a supercritical region occurring at generally higher temperatures and pressures. Operation above the critical point of a pressure/temperature diagram (supercritical phase) can offer advantages. In an aspect, polymerization can occur in an environment having a suitable combination of temperature and pressure.

In some aspects, a polymerization process as disclosed herein can comprise an olefin polymerization process conducted in the absence of added hydrogen. In such aspects, a catalyst system can be contacted with an olefin monomer and optionally an olefin comonomer in a polymerization reactor system under polymerization conditions to produce an olefin polymer, wherein the polymerization process is conducted in the absence of added hydrogen (no hydrogen is added to the polymerization reactor system). As will be appreciated by one of skill in the art, and with the help of this disclosure, hydrogen can be generated in-situ by catalyst compositions in various olefin polymerization processes, and the amount of hydrogen generated can vary depending upon the specific catalyst components employed, the type of polymerization process used, the polymerization reaction conditions utilized, and the like.

In other aspects, a polymerization process as disclosed herein can comprise an olefin polymerization process conducted in the presence of a suitable amount of added hydrogen. In such aspects, a catalyst system can be contacted with an olefin monomer and optionally an olefin comonomer in a polymerization reactor system under polymerization conditions to produce an olefin polymer, wherein the polymerization process is conducted in the presence of added hydrogen (hydrogen is added to the polymerization reactor system). For example, the ratio of hydrogen to the olefin monomer ($H_2$/MON) in the polymerization process can be controlled, often by the feed ratio of hydrogen to the olefin monomer entering the reactor. The added hydrogen to olefin monomer ratio in the process can be controlled at a weight ratio which falls within a range of from about 25 ppm to about 1500 ppm, alternatively from about 50 to about 1000 ppm, or alternatively from about 100 ppm to about 750 ppm.

In some aspects, the feed or reactant ratio of hydrogen to olefin monomer can be maintained substantially constant during the polymerization run for producing a particular polymer grade. That is, the hydrogen:olefin monomer ratio (e.g., $H_2$/MON) can be selected at a particular ratio within a range of from about 5 ppm up to about 1000 ppm or so, and maintained at the ratio to within about +/−25% during the polymerization run. For example, if the target $H_2$/MON ratio is 100 ppm, then maintaining the $H_2$/MON ratio substantially constant would entail maintaining the feed $H_2$/MON ratio between about 75 ppm and about 125 ppm. Further, the addition of comonomer (or comonomers) can be, and generally is, substantially constant throughout the polymerization run for producing a particular polymer grade.

However, in other aspects, it is contemplated that monomer, comonomer (or comonomers), optionally hydrogen, or combinations thereof can be periodically pulsed to the reactor, for instance, in a manner similar to that employed in U.S. Pat. No. 5,739,220; and U.S. Publication No. 2004/0059070; each of which is incorporated by reference herein in its entirety.

The concentration of the reactants entering the polymerization reactor system can be controlled to produce resins with certain physical and mechanical properties, such as the polymer resin disclosed herein or component thereof. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, SCB, long chain branching (LCB), and rheological measurements.

The concentrations, partial pressures, or both of monomer, comonomer, hydrogen, co-catalyst, modifiers, and electron donors are important in producing these resin properties. Comonomer can be used to control product density. Hydrogen can be used to control product molecular weight. Cocatalysts can be used to alkylate, scavenge poisons and control molecular weight. Modifiers can be used to control product properties and electron donors can affect stereoregularity, molecular weight distribution, molecular weight, or combinations thereof. In addition, the concentration of poisons should be minimized because poisons impact the reactions and product properties.

The olefin monomers suitable for use in the polymerization processes disclosed herein can comprise $C_2$ to $C_{30}$ olefin monomers, alternatively $C_2$ to $C_{20}$ olefin monomers, or alternatively $C_2$ to $C_{12}$ olefin monomers (e.g., ethylene, propylene, butene, pentene, 4-methyl-1-pentene, hexene, octene, decene, dodecene). In some aspects, the monomers can include olefinic unsaturated monomers, $C_4$ to $C_{18}$ diolefins, conjugated or nonconjugated dienes, polyenes, vinyl monomers, cyclic olefins, and the like. For example, in some aspects, the monomers can include norbornene, norbornadiene, isobutylene, isoprene, vinylbenzylcyclobutane, styrene, alkyl substituted styrene, ethylidene norbornene, dicyclopentadiene, cyclopentene, and the like.

In an aspect, the monomer comprises $C_2$ to $C_3$ olefin monomers. For example, the monomer comprises ethylene. In some aspects, the monomer comprises ethylene, wherein the produced polymer resin or component thereof comprises an ethylene homopolymer.

In other aspects, ethylene is copolymerized with a comonomer to produce a copolymer. Nonlimiting examples of comonomers suitable for use in the present disclosure include alpha olefins, such as propylene, 1-butene, 1-pentene, 1-hexene, 3-methyl-1-butene, 4-methyl-1-pentene, 1-heptene, 1-octene, 1-nonene, 1-decene, and the like, or combinations thereof. In an aspect, the comonomer comprises 1-hexene.

In an aspect, the comonomer can be introduced to the reactor (e.g., reaction zone) in an amount of from about 0.01 wt. % to about 10 wt. %, alternatively from about 0.01 wt. % to about 5 wt. %, or alternatively from about 0.1 wt. % to about 4 wt. %, based on the total weight of monomer and comonomer introduced to the reactor (e.g., reaction zone).

Any suitable polymerization catalyst system can be employed for the production of polymer resins or component thereof (e.g., unimodal polyolefins, multimodal polyolefins, bimodal polyolefins, trimodal polyolefins) as disclosed herein. A suitable polymerization catalyst system can comprise a catalyst and, optionally, a co-catalyst (e.g., an organoaluminum compound), a promoter, or both. In some aspects, the catalyst system can comprise an activator (e.g., activator-support). Nonlimiting examples of suitable catalyst systems include but are not limited to single-site or dual-site catalysts such as Ziegler Natta catalysts, Ziegler catalysts, chromium catalysts, chromium oxide catalysts, chrome-silica catalysts, chrome-titania catalysts, chromocene catalysts, metallocene catalysts, nickel catalysts, or combinations thereof. Suitable metallocene catalysts for use in the systems described herein can be any conventional or non-conventional metallocene catalyst. As used herein, the term "metallocene" is used to refer to all catalytically active metals: η-ligand complexes in which a metal is complexed by one, two, or more open chain or closed-ring η-ligands. The use of bridged bis-η-ligand metallocenes, single η-ligand "half metallocenes", and bridged η-σ ligand "scorpionate" metallocenes is preferred in accordance with some aspects of the present disclosure. The metal in such complexes is preferably a group 4A, 5A, 6A, 7A or 8A metal or a lanthanide or actinide of the Periodic Table of the Elements, especially a group 4A, 5A or 6A metal, more particularly Zr, Hf or Ti. The η-ligand preferably comprises $η^4$ or $η^5$ open-chain or a $η^5$-cyclopentadienyl ring, optionally with a ring or chain carbon replaced by a heteroatom (e.g., N, B, S or P), optionally substituted by pendant or fused ring substituents and optionally linked by bridge (e.g., a 1 to 4 atom bridge such as $(CH_2)_2$, $C(CH_3)_2$ or $Si(CH_3)_2$) to a further optionally substituted homo or heterocyclic cyclopentadienyl ring. The ring substituents can, for example, be halo atoms or alkyl groups optionally with carbons replaced by heteroatoms such as O, N and Si, especially Si and O and optionally substituted by mono or polycyclic groups such as phenyl or naphthyl groups. Catalyst systems suitable for use in the present disclosure have been described, for example, in U.S. Pat. Nos. 7,163,906; 7,619,047; 7,790,820; 7,960, 487; 8,138,113; 8,207,280; 8,268,944; 8,450,436; and 9,181,372; each of which is incorporated by reference herein in its entirety.

In an aspect of the present disclosure, the catalyst system can comprise an activator. The activator can be a solid oxide activator-support, a chemically treated solid oxide, a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, an aluminoxane, a supported aluminoxane, an ionizing ionic compound, an organoboron compound, or any combination thereof. The terms "chemically-treated solid oxide," "solid oxide activator-support," "acidic activator-support," "activator-support," "treated solid oxide compound," and the like are used herein to indicate a solid, inorganic oxide of relatively high porosity, which exhibits Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide compound comprises the calcined contact product of at least one solid oxide compound with at least one electron-withdrawing anion source compound. Typically, the chemically-treated solid oxide comprises at least one ionizing, acidic solid oxide compound. The terms "support" and "activator-support" are not used to imply these components are inert, and such components should not be construed as an inert component of the catalyst composition.

Catalyst systems suitable for use in the present disclosure, as well as suitable reactors and polymerization conditions are described in more detail in U.S. Pat. Nos. 8,268,944; 9,845,367; and 9,850,330; and EP No. 1756175; each of which is incorporated by reference herein in its entirety.

Monomers, such as ethylene, can be polymerized in the presence of the catalyst system (e.g., catalyst, cocatalyst). Polymerizing monomers can comprise allowing a polymerization reaction between a plurality of monomers by contacting a monomer or monomers with a catalyst system under conditions suitable for the formation of a polymer. Polymerizing comonomers can comprise allowing a polymerization reaction between a plurality of comonomers by contacting a comonomer or comonomers with a catalyst system under conditions suitable for the formation of a copolymer.

As disclosed herein, polymerizing monomers can comprise selectively manipulating one or more polymerization reaction conditions (e.g., process conditions) to yield a given polymer product (e.g., polymer resins or component thereof as disclosed herein), to yield a polymer product having one or more desirable properties, to achieve a desired efficiency, to achieve a desired yield, and the like, or combinations thereof. In an aspect, the method of producing polyolefins as disclosed herein can comprise adjusting one or more polymerization reaction conditions.

Polymerizing monomers can comprise maintaining a suitable temperature, pressure, partial pressure(s), or combinations thereof during the polymerization reaction; alternatively, cycling between a series of suitable temperatures, pressures, partial pressure(s), or combinations thereof during the polymerization reaction.

Polymerizing monomers can comprise introducing ethylene monomer, a comonomer, or both to one or more reaction zones. The concentration of each of the monomer and comonomer can be selectively manipulated for each individual reactor (e.g., reaction zone), to achieve a polyolefin with desired properties.

Polymerizing monomers can include introducing hydrogen into one or more of reactors (e.g., reaction zones). In some aspects, the amount of hydrogen introduced into each reaction zone can be adjusted so as to obtain, in the diluent, a molar ratio of hydrogen to ethylene (e.g., $H_2$/MON ratio) of 0.001 to 0.1. This molar ratio can be at least 0.004 in each reaction zone, and in some instances this molar ratio cannot exceed 0.05. In some aspects, the ratio of the concentration of hydrogen in the diluent in a first reaction zone to the concentration of hydrogen in a second reaction zone can be at least 20, alternatively, at least 30, alternatively, at least 40, alternatively, not greater than 300, or alternatively, not greater than 200. Suitable hydrogen concentration control methods and systems are disclosed in U.S. Pat. No. 6,225,421, which is incorporated by reference herein in its entirety.

Polymerizing monomers can comprise introducing a catalyst, a cocatalyst, or both to one or more reaction zones. The concentration of each of the catalyst and cocatalyst can be selectively manipulated for each individual reactor (e.g., reaction zone), to achieve a polyolefin with desired properties.

Polymerizing monomers can comprise circulating, flowing, cycling, mixing, agitating, or combinations thereof, the monomers (optionally, comonomers), catalyst system, reaction mixture (e.g., slurry) within one or more reaction zones, between one or more reaction zones, or combinations thereof. In aspects where the monomers (optionally, comonomers), catalyst system, reaction mixture (e.g., slurry), or combinations thereof are circulated, circulation can be at a velocity (e.g., slurry velocity) of from about 1 m/s to about 30 m/s, alternatively, from about 2 m/s to about 17 m/s, or alternatively, from about 3 m/s to about 15 m/s. As will be appreciated by one of skill in the art, and with the help of this disclosure, the circulation velocity directly correlates with the residence time in a particular reactor (e.g., reaction zone), and the residence time of each reactor (e.g., reaction zone) can be individually manipulated by adjusting the fluid velocity.

Polymerizing monomers can comprise configuring the one or more reaction zones to yield a multimodal (e.g., a bimodal, trimodal) polymer (e.g., polyethylene).

In an aspect, a method of producing a polymer resin or component thereof (e.g., polyethylene resin or component thereof) as disclosed herein can comprise polymerizing an olefin monomer in one or more reaction zones (e.g., a plurality of reaction zones) under polymerization conditions to form multimodal polyolefins; for example, to form multimodal polyolefins (e.g., multimodal polymer resin as disclosed herein) having a desired set of characteristics stemming from a desired composition (e.g., the composition of the analyzed polymer sample, as described by the identified and quantified polymer components). The desired set of characteristics can include any of a variety of properties, including but not limited to, density, short chain branching, crystallization temperature, melt index, high load melt index, molecular weight distribution, and the like, for example.

Herein, the "modality" of a polymer resin refers to the form of its molecular weight distribution curve, i.e., the appearance of the graph of the polymer weight fraction (w) as a function of its molecular weight (M). The polymer weight fraction refers to the weight fraction of molecules of a given size. A polymer having a molecular weight distribution curve showing a single peak can be referred to as a unimodal polymer, a polymer having a curve showing two distinct peaks can be referred to as bimodal polymer, a polymer having a curve showing three distinct peaks can be referred to as trimodal polymer, etc. A polymeric composition including a plurality of molecular weight peaks (e.g., 2 or more molecular weight peaks) is considered to be a multimodal polyolefin (e.g., bimodal polyolefin, trimodal polyolefin, and the like).

Multimodal polyolefins can be produced via a variety of processes. In some aspects, multimodal polyolefins can be produced via polymerization processes utilizing multimodal catalyst systems (i.e., catalyst systems including at least two different catalytically active metal components), for example in a single reaction zone, although more than one reaction zone can be used. Alternatively, multimodal polyolefins can be produced by employing at least two reaction zones, wherein each reaction zone can independently have its own set of polymerization conditions. Such reaction zones can be connected in series, wherein a transfer effluent from a reaction zone (e.g., a first reaction zone) can be transferred to a subsequent reaction zone (e.g., a second reaction zone), and so forth, until the multimodal polyolefin product is discharged from a final reaction zone with the desired set of characteristics.

In an aspect, a method of producing a polymer resin or component thereof (e.g., polyethylene resin or component thereof) as disclosed herein can comprise forming bimodal polyolefins. As used herein, the term "bimodal polyolefin" refers to a single polyolefin composition including at least one identifiable high molecular weight (BMW) fraction and at least one identifiable low molecular weight (LMW) fraction, for example two distinct peaks on a molecular weight distribution curve. In such aspect, the bimodal polyolefins can be produced by employing a first reaction zone connected in series to a second reaction zone, so that the transfer effluent withdrawn from the first reaction zone (which generally includes a first polyolefin and unreacted olefin monomer) can be introduced into the second reaction zone; and a polymerization product formed in the second reaction zone is withdrawn therefrom and includes the bimodal polyolefin. In the preparation of bimodal polyolefins, the BMW fraction and the LMW fraction can be prepared in any suitable order in the reaction zones, e.g., the LMW fraction can be formed in a first reaction zone and the BMW fraction in a second reaction zone, or vice versa, for example. The individual components of the multimodal polyolefin (e.g., bimodal polyolefin) can be obtained by deconvoluting a gel permeation chromatography (GPC) curve profile of the copolymer as described in U.S. Publication No. 20070298508 A1, which is incorporated by reference herein in its entirety.

In some aspects, the bimodal resin can have a BMW component and a LMW component; wherein the BMW component is present in an amount of from about 1 wt. % to about 99 wt. %, alternatively from about 5 wt. % to about 95 wt. %, alternatively from about 20 wt. % to about 80 wt. %, alternatively from about 30 wt. % to about 70 wt. %, alternatively from about 35 wt. % to about 65 wt. %, alternatively from about 40 wt. % to about 60 wt. %, alternatively from about 45 wt. % to about 55 wt. %, or alternatively about 50 wt. %; and wherein the LMW component is present in an amount of from about 99 wt. % to about 1 wt. %, alternatively from about 95 wt. % to about 5 wt. %, alternatively from about 80 wt. % to about 20 wt. %, alternatively from about 70 wt. % to about 30 wt. %, alternatively from about 65 wt. % to about 35 wt. %, alternatively from about 60 wt. % to about 40 wt. %, alternatively from about 55 wt. % to about 45 wt. %, or alternatively about 50 wt. %.

In some aspects, a comonomer (that is different from the olefin monomer) can also be introduced into the second reaction zone. For example, the comonomer can be a $C_4$-$C_8$ olefin monomer. In an aspect, the comonomer can comprise butene, hexene (e.g., 1-hexene), or both. In an aspect, the comonomer comprises 1-hexene.

The first reaction zone can generally be operated under first polymerization conditions, while the second reaction zone can generally be operated under second polymerization conditions. The first polymerization conditions and the second polymerization conditions can be adapted to form polyolefins having a desired set of characteristics. As such, the first polymerization conditions and the second polymerization conditions can vary from one another. However, it is contemplated that in certain circumstances the first and second polymerization conditions can be similar, if not the same. For example, in one or more aspects, the same catalyst system can be utilized in the plurality of reaction zones. However, in other aspects, different catalyst systems can be used in the plurality of reaction zones.

In some aspects, the polymerization process comprises polymer product separation. The separation can occur at any point within the process. For example, separation can occur after withdrawing the polymerization product from the second reaction zone, to recover a polymer resin or component thereof as disclosed herein, such as a polyethylene resin. Alternatively, the process can include separating a first reaction zone product, either within the transfer effluent or another stream withdrawn from the first reaction zone. Such separation can be accomplished by methods known in the art and can include, without limitation, concentration devices, such as hydrocyclones, flashing devices, or combinations thereof, for example. The transfer effluent or a portion thereof can be introduced to the second reaction zone with or without separation of its components.

In an aspect, the produced polyethylene resins or component thereof as disclosed herein can be characterized by a desired composition (e.g., the composition of the analyzed polymer sample, as described by the identified and quantified polymer components), as well as by desired properties, such as density, SCB, crystallization temperature, melt index, high load melt index, molecular weight distribution, and the like, or combinations thereof.

In an aspect, comparing the composition of the produced polyethylene resin with the desired composition (e.g., the composition of the analyzed polymer sample, as described by the identified and quantified polymer components) can provide for near real-time feedback to the one or more reaction zones. The term "near real-time," as used herein, refers to a delay that is introduced by automated data processing between the occurrence of an event (e.g., live event) and the use of processed data. For example, classifying an event as a near real-time event refers to the delay that allows the use of the processed data near the time of the live event, wherein such delay refers to the difference between the real-time event occurrence and the processing time. For example, the difference between the real-time event occurrence and the processing time can be less than 15 minutes (min), less than 30 min, less than 45 min, less than 1 hour (h), less than 2 h, less than 3 h, and the like. Further, such delay can refer to a time interval between when data are received for analysis and when analysis is performed and displayed on an electronic display screen (e.g., monitor screen, computer screen), wherein such time interval can be from less than about 1 min to less than about 10 min, or alternatively from about 3 seconds (s) to about 3 min.

The terms "real-time" or "actual real-time" as used herein can refer to the instantaneous data processing, wherein a measurement (e.g., measured item, measurement data) is transmitted and received at substantially the same time the measurement is occurring, e.g., data or information is instantaneously or nearly instantaneously streamed or transmitted. For example, the real-time data can be CCD data for the produced resin. As another example, the real-time data can be analysis data of the produced polymer resin with respect to its properties, such as desired properties, such as density, SCB, crystallization temperature, melt index, high load melt index, molecular weight distribution, and the like, or combinations thereof. CCD data and property analysis data can be provided substantially instantaneously (e.g., as soon as it is obtained), such as within about 2 seconds or less from the time the analysis or measurement is occurring, to a computer system or computer readable medium.

As will be appreciated by one of skill in the art, and with the help of this disclosure, while the processing of the data (e.g., resin CCD data, resin property data) can occur in real-time, the feedback to the reaction zone occurs in near real-time. Data processing can be instantaneous (i.e., real-time) data processing, wherein data (e.g., resin CCD data, resin property data) is transmitted and received at the same time the data processing is occurring, e.g., data or information is instantaneously or nearly instantaneously streamed or transmitted. The real-time data can be resin CCD data, resin property data, and the like, or combinations thereof, wherein the real-time data can be provided instantaneously (e.g., as soon as it is obtained) from an analysis system, a testing system, or combinations thereof to a control system, as will be described in more detail later herein.

As will be appreciated by one of skill in the art, and with the help of this disclosure, there is a time delay between the time when the reaction zone produces the resin, and the time the resin is tested for CCD and properties, and further the time when the CCD and properties data are transmitted from the analysis system, the testing system, or combinations thereof to the control system; which introduces a delay in the time when the reaction zone receives feedback about the properties of the produced resin (e.g., near real-time feedback). Generally, the processes for the production of multimodal polyethylene resin are continuous processes, and the produced resin is sampled and tested for CCD, properties, or combinations thereof at various time intervals during the production process, such as every 15 min, every 30 min, every 45 min, every 1 h, every 2 h, every 3 h, and the like. Further, and as will be appreciated by one of skill in the art, and with the help of this disclosure, such resin sampling, analysis and testing can provide for near real-time feedback about resin CCD and properties to the reaction zones, in the context of the entire life time of the production process (e.g., continuous production process).

As will be appreciated by one of skill in the art, and with the help of this disclosure, the value of desired composition and properties (e.g., density, SCB, crystallization temperature, melt index, high load melt index, molecular weight distribution, and the like, or combinations thereof) correlates with a variety of operational parameters, such as ethylene concentration, comonomer concentration, $H_2$/MON ratio, temperature, catalyst concentration, cocatalyst concentration, pressure, residence time, reactor solids concentration, and the like, or combinations thereof. In some aspects, a single operational parameter (e.g., ethylene concentration, comonomer concentration, $H_2$/MON ratio, temperature, catalyst concentration, cocatalyst concentration, pressure, residence time, reactor solids concentration, and the like) can be changed in at least one reactor to help drive a resin product to meet desired specifications (e.g., desired composition and properties). In other aspects, two or more operational parameters (e.g., ethylene concentration, comonomer concentration, $H_2$/MON ratio, temperature, catalyst concentration, cocatalyst concentration, pressure, residence time, reactor solids concentration, and the like, or combinations thereof) can be changed (e.g., concerted change of operational parameters) in at least one reactor to help drive a resin product to meet desired specifications (e.g., desired composition and properties).

In an aspect, the produced polymer resin (e.g., produced polyethylene resin) can be processed by any suitable process or series of processes configured to produce a polymer product as can be suitable for commercial or industrial usage, storage, transportation, further processing, or combinations thereof.

In an aspect, a method of recycling a polymer resin can comprise (a) analyzing a polymer resin as disclosed herein to yield identified polymer components and quantified polymer components; and (b) recycling at least a portion of the polymer resin having two or more identified and quantified polymer components.

In some aspects, polymers or components thereof may be subjected to mechanical recycling, wherein mechanical recycling may be used for the recovery of pre-consumer (e.g., post-industrial) materials, as well as for the recovery of post-consumer plastic waste. Generally, mechanical recycling refers to operations that aim to recover plastics by mechanical processes (e.g., grinding, washing, separating, drying, re-granulating and compounding), thus producing a mechanically processed product that can be converted into recycled plastics products. Mechanical recycling is also known as material recycling, material recovery or, as related to plastics, back-to-plastics recycling. In mechanical recycling, plastic waste (e.g., sorted by material type) can be milled and washed, passed through a flotation separation, and dried. The resulting plastic flakes can then be either used directly to produce new plastic materials or can be further processed into granulates.

In other aspects, polymers or components thereof may be subjected to chemical recycling. Generally, chemical recycling refers to a process of reducing polymers or components thereof to their chemical building-blocks (e.g., monomers, recovered monomers), which recovered monomers can then be polymerized back into fresh plastics. Chemical recycling can be any process by which a polymer is chemically reduced to its original monomer form so that it can eventually be processed (re-polymerized) and remade into new plastic materials that go on to be new plastic products.

In some aspects, a method of recycling a polymer resin can comprise analyzing a polymer resin as disclosed herein via aTREF to yield identified polymer components and quantified polymer components.

In other aspects, a method of recycling a polymer resin can comprise analyzing a polymer resin via Fourier-transform infrared (FTIR) spectroscopy to yield identified polymer components and quantified polymer components. For example, the polymer resin (e.g., at least a portion of the polymer sample) can be subjected to FTIR spectroscopy to yield an FTIR spectrum; wherein the FTIR spectrum can provide for identifying the two or more polymer components of the polymer sample to yield two or more identified polymer components. In such aspects, the identifying may comprise comparing the FTIR spectrum with an identification library that comprises a plurality of known polymer FTIR spectra, wherein each of the plurality of known polymer FTIR spectra is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof. In such aspects, the method may further comprise quantifying an amount of each of the two or more identified polymer components in the polymer sample to yield two or more quantified polymer components, wherein the quantifying comprises chemometric analysis of the FTIR spectrum. Chemometric analysis of the FTIR spectrum is similar to the chemometric analysis of the aTREF elution trace as described herein.

In an aspect, recycling the polymer resin can comprise (i) separating the two or more quantified polymer components from the polymer resin to yield two or more separated polymer components, (ii) forming at least a portion of the polymer resin, at least a portion of the two or more separated polymer components, or both at least a portion of the polymer resin and at least a portion of the two or more separated polymer components into an article, (iii) using at least a portion of the polymer resin, at least a portion of the two or more separated polymer components, or both at least a portion of the polymer resin and at least a portion of the two or more separated polymer components as a pyrolysis feedstock, gasification feedstock, combustion feedstock, or combinations thereof, or (iv) any combination of (i)-(iii).

In some aspects, subsequent to identifying and quantifying the polymer components in a polymer sample, the polymer resin can be separated into its individual components to yield two or more separated polymer components. The two or more separated polymer components may be further processed independently of each other, wherein each of the two or more separated polymer components can be formed into an article; used as a pyrolysis feedstock, gasification feedstock, combustion feedstock, or combinations thereof; combined with other polymers to form a resin having a desired composition; or combinations thereof.

In other aspects, the polymer resin can be processed without separating any components thereof, wherein the polymer resin can be formed into an article; used as a pyrolysis feedstock, gasification feedstock, combustion feedstock, or combinations thereof; combined with other polymers to form a resin having a desired composition; or combinations thereof.

Generally, pyrolysis refers to the thermal decomposition of materials in an inert atmosphere (e.g., in the absence of air or oxygen), whereby pyrolysis products are produced. For example, pyrolysis may comprise the thermal decomposition of the volatile components of an organic substance (e.g., polymers or components thereof). Pyrolysis encompasses thermal cracking and condensation reactions. Pyrolysis products can be grouped in pyrolysis gas (e.g., syngas), which contains un-condensable low molecular gases; pyrolysis liquids or oils, which contain condensable volatile compounds; and char, which is a solid residue. Compared to a combustion (e.g., incineration) process, which is relatively highly exothermic, pyrolysis is relatively endothermic. Pyrolysis typically uses an indirect heat source, and is conducted in a temperature range of about 400-1,400° F. (200-760° C.). Pyrolysis is widely used in chemical industries to produce charcoal, and methanol.

Gasification generally occurs in a relatively higher (by comparison to pyrolysis) temperature range of about 900-3,000° F. (480-1,650° C.) with very little air or oxygen (e.g., controlled amount of oxygen or steam). In addition to the thermal decomposition of the volatile components of the substance subjected to gasification (e.g., fossil fuel, polymers or components thereof), the non-volatile carbon char that would remain from pyrolysis is converted to additional gas, such as syngas. Steam may also be added to a gasifier to convert the carbon in the char to syngas. Gasification uses only a fraction of the oxygen that would be needed to burn (e.g., combust in an oxygen-rich atmosphere, such as air) the material. Heat during gasification can be supplied directly by partial oxidation of the carbon in the feedstock, and ash remains as a residual solid product of gasification. Ash produced in the gasification is a non-combustible material which contains a relatively low level of carbon.

Gasification can be regarded as a process intermediate between pyrolysis and combustion (e.g., incineration) in that gasification involves the partial oxidation of a substance (e.g., polymers or components thereof). This means that oxygen is added but the amounts are not sufficient to allow the fuel to be completely oxidized and full combustion to occur during gasification. The temperatures employed during gasification are typically above about 650° C. The process of gasification is largely exothermic, but some heat may be required to initialize and sustain the gasification process. The main product of gasification is a syngas, which contains carbon monoxide, hydrogen and methane. Typically, the gas generated from gasification can have a net calorific value (NCV) of MJ/Nm$^3$. For reference, the calorific value of syngas from pyrolysis and gasification is far lower than that of natural gas, which has an NCV of around 38 MJ/Nm$^3$.

Incineration or combustion usually involves the combustion of materials (e.g., fuel, unprepared (raw or residual) MSW (municipal solid waste), polymers or components thereof) in the presence of atmospheric air or sometimes only by oxygen alone; wherein the heat energy produced by combustion is usually converted into an useful form of work. To allow the combustion to take place, a sufficient quantity of oxygen is required to fully oxidize the fuel. Typically, incineration plant combustion (flame) temperatures are in excess of 850° C. and the combustible material (e.g., polymers or components thereof) is converted into carbon dioxide and water. Any noncombustible materials (e.g. metals, glass) remain as a solid, known as bottom ash, which contains a relatively small amount of residual carbon.

In an aspect, a system for analyzing a polymer resin (e.g., polyethylene resin) as disclosed herein can comprise an analytical instrument comprising an aTREF column and an IR detector; wherein the aTREF column is configured to receive a polymer sample solution (e.g., polyethylene sample solution), wherein the polymer sample solution comprises a polymer sample (e.g., a polyethylene sample) of the polymer resin and an aTREF solvent, wherein the polymer sample comprises two or more polymer components (e.g., two or more polyethylene components); wherein the aTREF column is configured to elute the two or more polymer components at different elution rates along the aTREF column to produce an aTREF eluent; and wherein the IR detector is configured to detect the two or more polymer components in the aTREF eluent and yield an aTREF elution trace; and a computer system configured to receive the aTREF elution trace from the analytical instrument, wherein the computer system comprises at least one processor; wherein the at least one processor compares the aTREF elution trace with an identification library and identifies the two or more polymer components of the polymer sample to yield two or more identified polymer components (e.g., two or more identified polyethylene components); wherein the identification library comprises a plurality of known polymer aTREF elution traces (e.g., a plurality of known polyethylene aTREF elution traces), wherein each of the plurality of known polymer aTREF elution traces is correlated with a known polymer component (e.g., known polyethylene component), wherein the known polymer component is characterized by an identifying parameter, and wherein the identifying parameter is selected from the group consisting of density, SCB, crystallization temperature, melt index, high load melt index, molecular weight distribution, and combinations thereof; and wherein the at least one processor performs quantification chemometric analysis of the aTREF elution trace to quantify an amount of each of the two or more identified polymer components in the polymer sample to yield two or more quantified polymer components (e.g., two or more quantified polyethylene components).

In an aspect, the system for analyzing a polymer resin as disclosed herein can further comprise a recycling system, wherein the recycling system is configured to receive the polymer resin, subsequent to identifying and quantifying the two or more polymer components. In some aspects, the recycling system can further comprise a separation system configured to separate the polymer resin into its individual components to yield two or more separated polymer components. In other aspects, the recycling system can further comprise a shaping system configured to form at least a portion of the polymer resin or separated component thereof into a shaped article. In yet other aspects, the recycling system can be configured to feed at least a portion of the polymer resin or separated component thereof to a pyrolysis unit, a gasification unit, a combustion unit, or combinations thereof.

In an aspect, the system for analyzing a polymer resin as disclosed herein can further comprise a polymerization reactor, wherein the polymerization reactor is configured to polymerize one or more monomers (e.g., ethylene) to produce the polymer resin (e.g., polyethylene resin); wherein the reactor operates under a plurality of polymerization conditions comprising monomer concentration, comonomer concentration, hydrogen to monomer ratio, temperature, catalyst concentration, cocatalyst concentration, pressure, residence time, reactor solids concentration, or combinations thereof; and a control system configured to receive the amount of each of the two or more identified polymer components (e.g., two or more identified polyethylene components) in the polymer sample (e.g., polyethylene sample) from the computer system, wherein the control system comprises at least one controller; and wherein the at least one controller adjusts at least one of the plurality of polymerization conditions in order to produce the desired polymer resin or component thereof. In such aspect, the system can further comprise a shaping system configured to receive the polymer resin (e.g., polyethylene resin) from the polymerization reactor, wherein the shaping system is configured to form at least a portion of the polymer resin into a shaped article. The control system can provide for near real-time feedback to the polymerization reactor.

In an aspect, the control system can comprise at least one processor (e.g., computer) and at least one controller (e.g., actuator). Generally, a control system is a device, or set of devices (e.g., at least one processor and at least one controller) that manages, commands, directs or regulates the behavior of other devices or systems (e.g., polyethylene production equipment or machines, such as a device for introducing a catalyst system component to a reaction zone, a device for introducing a reactant (e.g., monomer, comonomer, hydrogen) to a reaction zone, a temperature controller, and the like).

In an aspect, the control system can be a distributed control system (DCS). Generally, a DCS is a control system for a process (e.g., polymer production process, polyethylene production process) or plant (e.g., polymer production plant, polyethylene production plant), wherein control elements are distributed throughout the control system (as opposed to non-distributed control systems, which use a single controller at a central location). DCS controllers can be connected by communications networks for command and monitoring.

The analyzed polymer resin or separated component thereof, the produced polymer resin, or both the analyzed polymer resin or separated component thereof and the produced polymer resin can be routed to a shaping system comprising a polymer processor. The polymer processor can be configured for the performance of a suitable processing means (e.g., to form various articles), nonlimiting examples of which include cooling, injection molding, melting, pelletizing, film blowing, cast film, blow molding, extrusion, extrusion molding, rotational molding, thermoforming, cast molding, fiber spinning, and the like, or combinations thereof. Various additives and modifiers can be added to the polymer resin or component thereof to provide better processing during manufacturing and for desired properties in the end-use product. Nonlimiting examples of such additives can include surface modifiers such as slip agents, antiblocks, tackifiers; antioxidants such as primary and secondary antioxidants; pigments; processing aids such as waxes/oils and fluoroelastomers; special additives such as fire retardants, antistats, scavengers, absorbers, odor enhancers, and degradation agents; or combinations thereof.

The processed resin can include other suitable additives. Such additives can be used singularly or in combination and can be included in the resin before, during or after preparation of the resin as disclosed herein. Such additives can be added via known techniques, for example during an extrusion or compounding step, such as during pelletization or subsequent processing into an end-use article.

The polymer processor can be configured to form a suitable resin product. Nonlimiting examples of suitable resin products as can result from processing the polyethylene resin include films, powders, pellets, resins, liquids, or any other suitable form as will be appreciated by those of skill in the art. Such a suitable output can be for use in, for example, one or more of various consumer or industrial products. For example, the resin product can be utilized in any one or more of various articles (e.g., shaped articles), including, but not limited to, bottles, drums, toys, containers, household containers, utensils, film products, single layer film, multilayer film, tanks, fuel tanks, pipes, membranes, geomembranes, and liners. The polymer processor can be configured to form pellets for transportation to a consumer product manufacturer.

In some aspects, the shaping system can be configured to receive the polymer resin (e.g., polyethylene resin) and process the polymer resin into a film. In such aspects, the polymer resin can be a bimodal resin.

In some aspects, the shaping system can be configured to receive the polymer resin (e.g., polyethylene resin) and process the polymer resin into a pipe. In such aspects, the polymer resin can be a bimodal resin.

Referring to FIG. 1, a method 100 of analyzing a polymer resin 11 can comprise (a) a step 10 of providing a polymer sample of the polymer resin, wherein the polymer sample comprises two or more polymer components; (b) a step 20 of subjecting at least a portion of the polymer sample to analytical temperature rising elution fractionation (aTREF) analysis to yield an aTREF elution trace; (c) a step 30 of identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; and (d) a step 40 of quantifying an amount of each of the two or more identified polymer components in the polymer sample to yield two or more quantified polymer components, wherein the quantifying comprises chemometric analysis of the aTREF elution trace.

In some aspects, the method 100 of analyzing a polymer resin 11 can further comprise recycling 50 at least a portion of the polymer resin 11 having two or more polymer components identified according to step 30 and quantified according to step 40, wherein the identified composition of the polymer resin 11 is used to inform 50*a* the recycling step 50 (e.g., knowing the composition of the polymer resin 11 allows for deciding the suitability of the resin for a particular recycling process).

In other aspects, the method 100 of analyzing a polymer resin 11 can further comprise separating 60 the two or more quantified polymer components from at least a portion of the polymer resin 11 to yield two or more separated polymer components, wherein the identified composition of the polymer resin 11 is used to inform 60*a* the separating step 60 (e.g., knowing the composition of the polymer resin 11 allows for deciding the suitability of the resin for a particular separation process).

In yet other aspects, the method 100 of analyzing a polymer resin 11 can further comprise a step 70 of selecting one or more monomers that can form the two or more identified polymer components; and polymerizing the one or more monomers to produce the polymer resin; wherein the polymerizing occurs under a plurality of polymerization conditions; and wherein each polymerization condition of the plurality of polymerization conditions is selected responsive 70*a* to step 40 from the group consisting of monomer concentration, comonomer concentration, hydrogen to monomer ratio, temperature, catalyst concentration, cocatalyst concentration, pressure, residence time, reactor solids concentration, and combinations thereof.

In still yet other aspects, the method 100 of analyzing a polymer resin 11 can further comprise, responsive 80*a* to step 40, a step 80 of selecting the two or more polymer components; and blending the selected two or more polymer components to produce the polymer resin.

In an aspect, the method 100 of analyzing a polymer resin 11 can further comprise a step 90 of (i) forming at least a portion of the polymer resin, at least a portion of the two or more separated polymer components, or both at least a portion of the polymer resin and at least a portion of the two or more separated polymer components into an article; (ii) using at least a portion of the polymer resin, at least a portion of the two or more separated polymer components, or both at least a portion of the polymer resin and at least a portion of the two or more separated polymer components as a pyrolysis feedstock, gasification feedstock, combustion feedstock, or combinations thereof; or (iii) both (i) and (ii).

In an aspect, the method of analyzing a polymer resin described with respect to FIG. 1 can be implemented on a computer. A control scheme (e.g., a control scheme for identifying one or more components in a resin; a control scheme for quantifying one or more components in a resin; a control scheme for selecting one or more monomers to polymerize and produce the resin; a control scheme for selecting one or more polymer components to blend and form the resin; a control scheme for a feed-back loop to a reaction zone) implemented by a control system as disclosed herein can be in the form of hard coded instructions or as a software module stored in a memory and executed by a processor of a computer. Further, any of the functions described with respect to the control systems disclosed herein can be implemented on a computer or in another system as described herein.

Figure 2:
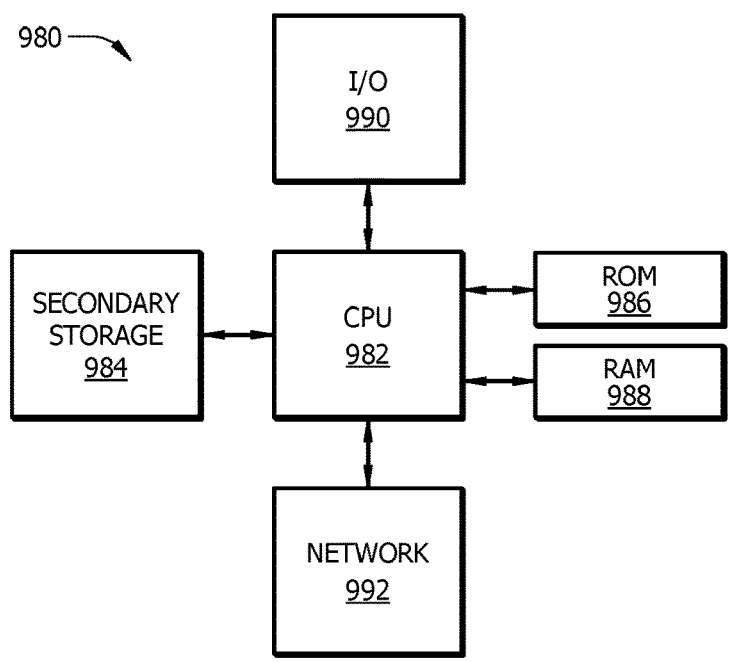
FIG. 2 illustrates a schematic layout of a computer system.

FIG. 2 illustrates a computer system 980 suitable for implementing one or more aspects disclosed herein. The computer system 980 includes a processor 982 (which may be referred to as a central processor unit or CPU) that is in communication with memory devices including secondary storage 984, read only memory (ROM) 986, random access memory (RAM) 988, input/output (I/O) devices 990, and network connectivity devices 992. The processor 982 may be implemented as one or more CPU chips.

It is understood that by programming and/or loading executable instructions onto the computer system 980, at least one of the CPU 982, the RAM 988, and the ROM 986 are changed, transforming the computer system 980 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by design rules known to those skilled in the art, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 984 is typically comprised of one or more disk drives or tape drives and is used for non-volatile storage of data and as an over-flow data storage device if RAM 988 is not large enough to hold all working data. Secondary storage 984 may be used to store programs which are loaded into RAM 988 when such programs are selected for execution. The ROM 986 is used to store instructions and perhaps data which are read during program execution. ROM 986 is a non-volatile memory device which typically has a small memory capacity relative to the larger memory capacity of secondary storage 984. The RAM 988 is used to store volatile data and perhaps to store instructions. Access to both ROM 986 and RAM 988 is typically faster than to secondary storage 984. The secondary storage 984, the RAM 988, and/or the ROM 986 may be referred to in some contexts as computer readable storage media and/or non-transitory computer readable media.

I/O devices 990 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 992 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 992 may enable the processor 982 to communicate with the Internet or one or more intranets. With such a network connection, it is contemplated that the processor 982 might receive information from the network, or might output information to the network in the course of performing the above-described method steps. Such information, which is often represented as a sequence of instructions to be executed using processor 982, may be received from and outputted to the network, for example, in the form of a computer data signal embodied in a carrier wave.

Such information, which may include data or instructions to be executed using processor 982 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 982 executes instructions, codes, computer programs, scripts which it accesses from hard disk, floppy disk, optical disk (these various disk based systems may all be considered secondary storage 984), ROM 986, RAM 988, or the network connectivity devices 992. While only one processor 982 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 984, for example, hard drives, floppy disks, optical disks, and/or other device, the ROM 986, and/or the RAM 988 may be referred to in some contexts as non-transitory instructions and/or non-transitory information.

In an aspect, the computer system 980 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an aspect, virtualization software may be employed by the computer system 980 to provide the functionality of a number of servers that is not directly bound to the number of computers in the computer system 980. For example, virtualization software may provide twenty virtual servers on four physical computers. In an aspect, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an aspect, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 980, at least portions of the contents of the computer program product to the secondary storage 984, to the ROM 986, to the RAM 988, and/or to other non-volatile memory and volatile memory of the computer system 980. The processor 982 may process the executable instructions and/or data structures in part by directly accessing the computer program product, for example by reading from a CD-ROM disk inserted into a disk drive peripheral of the computer system 980. Alternatively, the processor 982 may process the executable instructions and/or data structures by remotely accessing the computer program product, for example by downloading the executable instructions and/or data structures from a remote server through the network connectivity devices 992. The computer program product may comprise instructions that promote the loading and/or copying of data, data structures, files, and/or executable instructions to the secondary storage 984, to the ROM 986, to the RAM 988, and/or to other non-volatile memory and volatile memory of the computer system 980.

In some contexts, the secondary storage 984, the ROM 986, and the RAM 988 may be referred to as a non-transitory computer readable medium or a computer readable storage media. A dynamic RAM embodiment of the RAM 988, likewise, may be referred to as a non-transitory computer readable medium in that while the dynamic RAM receives electrical power and is operated in accordance with its design, for example during a period of time during which the computer 980 is turned on and operational, the dynamic RAM stores information that is written to it. Similarly, the processor 982 may comprise an internal RAM, an internal ROM, a cache memory, and/or other internal non-transitory storage blocks, sections, or components that may be referred to in some contexts as non-transitory computer readable media or computer readable storage media.

One or more of the disclosed systems, processes, or both for analyzing, recycling, producing, or combinations thereof polymer resins (e.g., polyolefins) can advantageously display improvements in one or more system characteristics, process characteristics, or both when compared to conventional systems, processes, or both for analyzing, recycling, producing, or combinations thereof polymer resins.

In an aspect, the disclosed systems, processes, or both for analyzing, recycling, producing, or combinations thereof polymer resins (e.g., polyolefins) can advantageously allow for the quantification of components in polymer resin samples, in addition to identifying such components; thereby providing invaluable insight into polymer samples that could be used for recycling polymers, production of polymers with specific properties, or both for recycling and producing polymers. Recycling and/or use as a pyrolysis feedstock, gasification feedstock, combustion feedstock, or combinations thereof for spent plastics (e.g., polymers, such as PE) can advantageously enhance their environmental sustainability. When plastics complete their use phase, they can advantageously be either recycled, or if this is not economic or environmentally beneficial, they can be used as a pyrolysis feedstock, gasification feedstock, or incinerated to provide a source of energy.

In an aspect, the disclosed systems, processes, or both for analyzing, recycling, producing, or combinations thereof polymer resins (e.g., polyolefins) can advantageously allow for the quantification of components in polymer resin samples, wherein the quantified component may be present in the resin sample in an amount of less than about 99.9 wt. %, alternatively less than about 99.8 wt. %, alternatively less than about 99.5 wt. %, alternatively less than about 99 wt. %, alternatively less than about 95 wt. %, alternatively less than about 90 wt. %, alternatively less than about 80 wt. %, alternatively less than about 70 wt. %, alternatively less than about 60 wt. %, alternatively less than about 50 wt. %, alternatively less than about 40 wt. %, alternatively less than about 30 wt. %, alternatively less than about 20 wt. %, alternatively less than about 10 wt. %, alternatively less than about 5 wt. %, alternatively less than about 1 wt. %, alternatively less than about 0.5 wt. %, alternatively less than about 0.2 wt. %, or alternatively less than about 0.1 wt. %, based on the total weight of the polymer resin sample. Additional advantages of the systems, processes, or both for analyzing, recycling, producing, or combinations thereof polymer resins (e.g., polyolefins) as disclosed herein can be apparent to one of skill in the art viewing this disclosure.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

For all Examples herein, analytical temperature rising elution fractionation (aTREF) was conducted as follows on an aTREF instrument, PolymerChar TREF 200+. 40 mg of the polymer sample was manually loaded into a vessel. The instrument then charged 20 mL of 1,2,4-trichlorobenzene (TCB) into a vessel for sample dissolution at 150° C. for 1 hr. After dissolving the polymer, an aliquot (500 microliters) of the polymer solution was loaded on the column (stainless steel shots) at 150° C. and stabilized at 110° C. (cooling rate 10° C./min) for 10 minutes before cooling at 0.5° C./min to 35° C. Then, the elution was run at 0.5 mL/min TCB flow rate. There was 10 min of flow at 35° C. before starting a heating rate of 1° C./min up to 120° C. Analysis of the elution solution was done by an IR detector. The peak aTREF temperature is the location of the highest point of the aTREF curve. The area under the curve corresponds to the weight percentage of material coming off.

Example 1

The ability of aTREF to resolve between different types of linear low density polyethylene (LLDPE) was investigated. Polymer blends were made with two different types of LLDPE in order to produce films: a metallocene-catalyzed LLDPE (mLLDPE) and a Ziegler-Natta-catalyzed (ZN-LLDPE), wherein the composition of the blends is displayed in Table 1.

TABLE 1

| Blend Composition for Film |
| --- |
| 100% mLLDPE |
| 20% ZN-LLDPE + 80% mLLDPE |
| 40% ZN-LLDPE + 60% mLLDPE |
| 60% ZN-LLDPE + 40% mLLDPE |
| 80% ZN-LLDPE + 20% mLLDPE |
| 90% ZN-LLDPE + 10% mLLDPE |
| 100% ZN-LLDPE |

GPC data was recorded using an Agilent PL220 High-Temperature GPC Systems equipped with a Polymer Char IR4 detector. Samples were dissolved in 1,2,4-trichlorobenzene (TCB) at 150° C. to form a 1 mg/mL solution. A 400 µL sample injection volume of the solution was separated on three Styragel® HMW 6E columns (Waters, 12-20 µm pore size, 7.8 mm×300 mm) at a flow rate of 1.0 mL/min and temperature of 145° C.

Figure 3:
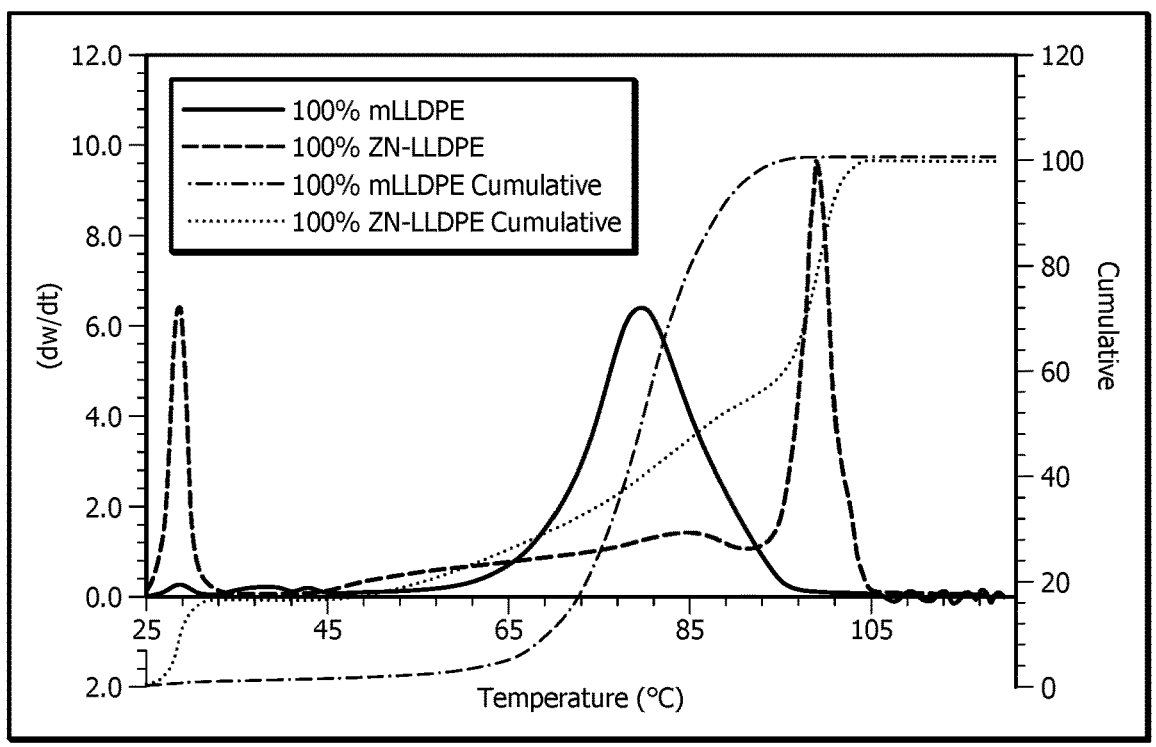
FIG. 3 displays analytical temperature rising elution fractionation (aTREF) elution traces for two different types of linear low density polyethylene (LLDPE)
Figure 4:
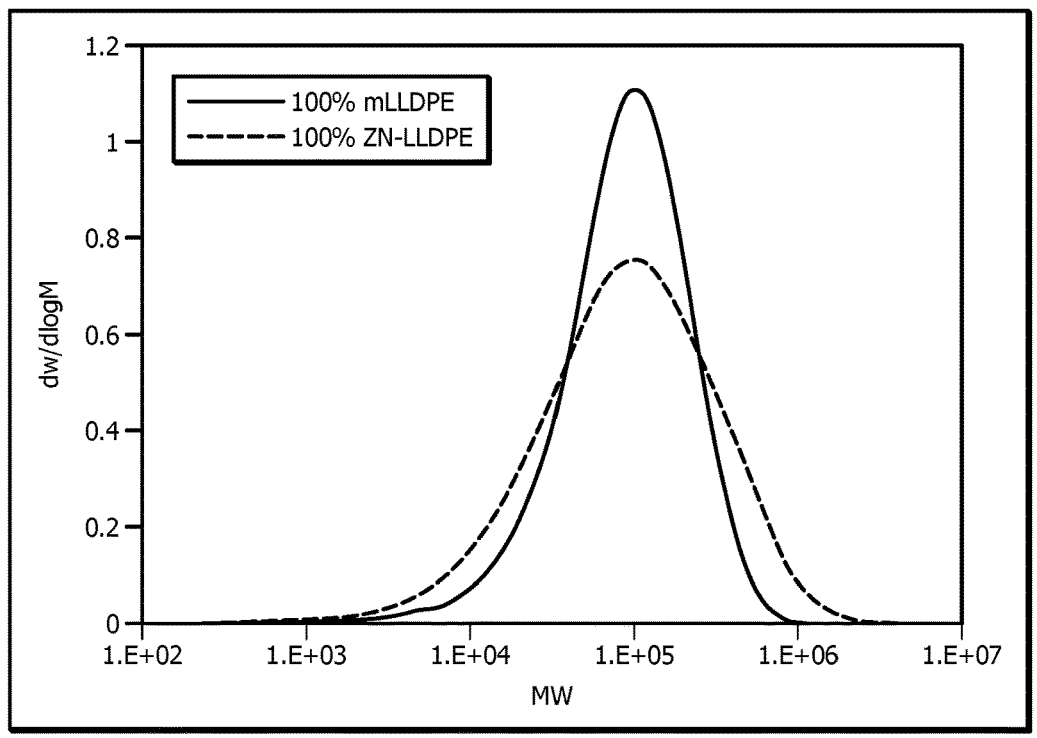
FIG. 4 displays gel permeation chromatography (GPC) curve profiles for two different types of LLDPE.

The starting resins (100%, no blend) have unique elution traces in the aTREF, as shown in FIG. 3, and reflect the chemical composition of the un-blended resin. ZN-LLDPE has a broader molecular weight distribution (MWD) than mLLDPE as a result of the catalyst used, as can be seen in FIG. 4. Both ZN-LLDPE and mLLDPE are low density resins. ZN-LLDPE has a density of 0.919 g/cc. The density of mLLDPE is 0.914 g/cc. However, the branching distribution is different. The branching increases across the MWD in ZN-LLDPE and is uniform across the distribution for mLLDPE. The aTREF data in FIG. 3 show the ZN-LLDPE contains higher crystalline material content than the mLLDPE as seen by the peak at 97.5° C., thereby enabling aTREF to distinguish between un-blended ZN-LLDPE and un-blended mLLDPE.

Example 2

The ability of aTREF to resolve (e.g., identify and quantify the different polymer components) between different types of LLDPE blended with each other and formed into a film was investigated. Polymer blends were made with two different types of LLDPE in order to produce films: mLLDPE and ZN-LLDPE, wherein the composition of the films, as well as aTREF elution trace data are displayed in Table 2.

TABLE 2

| Sample # | Type | Peak 1 | Area 1 | Peak 2 | Area 2 | Peak 3 | Area 3 | Peak 4 | Area 4 |
|---|---|---|---|---|---|---|---|---|---|
| 1 | 100% mLLDPE | 78.7 | 97.9 | 0.0 | 0.0 | 0.0 | 0.0 | 0.0 | 0.0 |
| 2 | 20% ZN-LLDPE + 80% mLLDPE | 54.7 | 2.8 | 56.6 | 1.3 | 78.6 | 80.2 | 97.1 | 12.8 |
| 3 | 40% ZN-LLDPE + 60% mLLDPE | 54.1 | 3.1 | 61.6 | 1.2 | 78.7 | 66.6 | 97.5 | 21.3 |
| 4 | 60% ZN-LLDPE + 40% mLLDPE | 43.2 | 1.4 | 57.1 | 3.0 | 78.4 | 55.0 | 97.8 | 28.5 |
| 5 | 80% ZN-LLDPE + 20% mLLDPE | 48.8 | 2.0 | 52.3 | 1.4 | 57.1 | 2.7 | 59.5 | 81.0 |
| 6 | 90% ZN-LLDPE + 10% mLLDPE | 67.3 | 13.1 | 79.4 | 15.7 | 89.1 | 12.1 | 97.9 | 41.2 |
| 7 | 100% ZN-LLDPE | 64.5 | 12.3 | 81.5 | 9.6 | 83.8 | 8.5 | 98.1 | 44.9 |
| 8 | 100% mLLDPE pellet | 78.8 | 97.5 | 0.0 | 0.0 | 0.0 | 0.0 | 0.0 | 0.0 |

Figure 5:
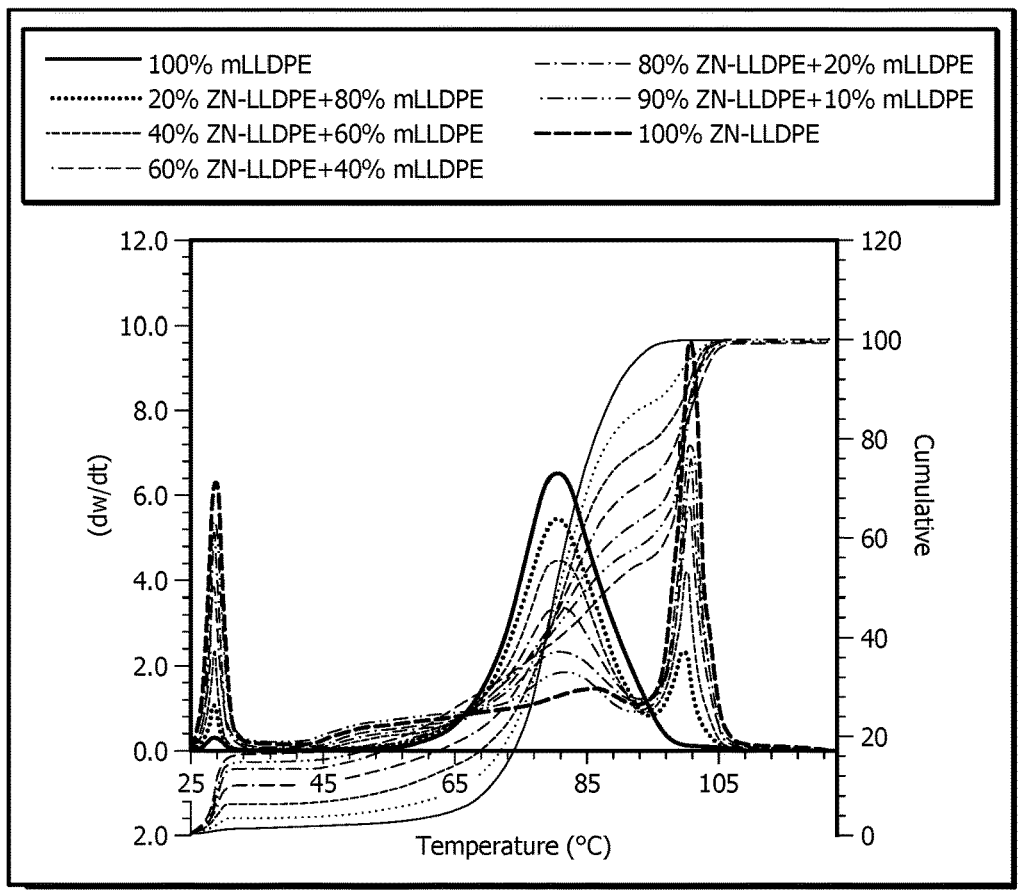
FIG. 5 displays aTREF elution traces for films containing varying amounts of two different types of LLDPE.

The contributions of each of the resins is visible in the aTREF elution traces, as shown in FIG. 5, even though some co-crystallization occurred between the two resins. The highly crystalline material in the ZN-LLDPE is clearly visible throughout the samples. The prominent lower elution temperature peak of the mLLDPE can clearly be seen in each of the blends in FIG. 5.

Example 3

The aTREF elution trace data acquired in Example 2 was subjected to further analysis as follows, in order to determine the suitability of chemometric analysis as disclosed herein for identifying and quantifying components in a polymer sample. The aTREF elution trace data from Example 2 was reconfigured to fit the requirements of the chemometric software Stand Alone Chemometrics Software (Solo) from Eigenvector Research Inc. for principle components analysis (PCA) and partial least squares (PLS) modeling. In order to reconfigure the data, the data for each sample were interpolated to ensure the variables, in this example the elution temperatures, were the same for each sample. The spectra were interpolated between 25-115° C. using 0.25° C. increments. The data for the aTREF traces were used, but not the cumulative curves. This reconfiguration yielded a 7×363 matrix.

Figure 6:
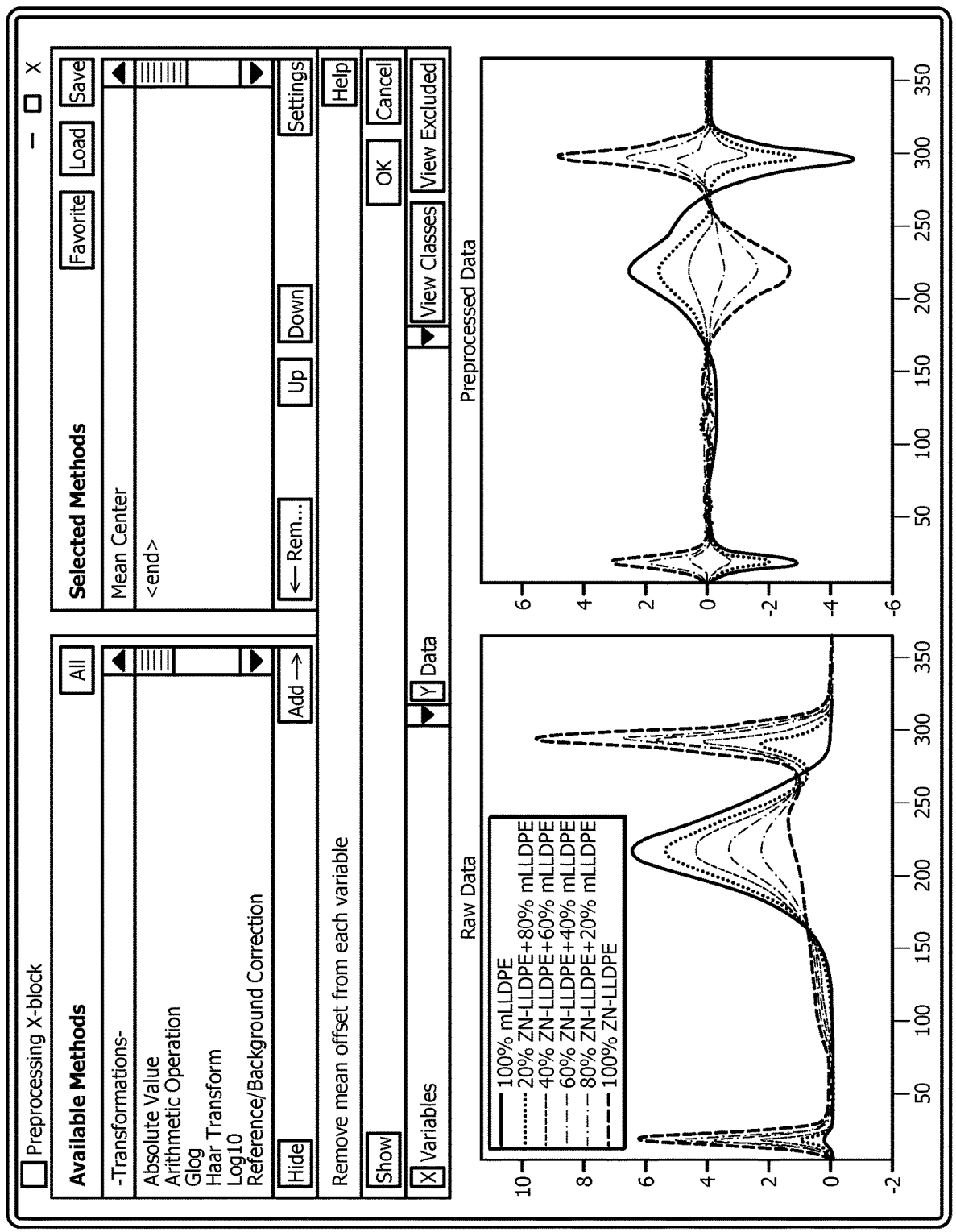
FIG. 6 displays the pre-processing of aTREF elution trace data in Stand Alone Chemometrics Software (Solo) software for principle components analysis (PCA)

The reconfigured data was loaded into Solo and subjected to PCA modeling. In setting up the analysis, the 90% ZN-LLDPE+10% mLLDPE sample #6 was left out of the calibration set to be used in the validation set. The aTREF data was inputted for the x-block and mean centered selected for the preprocessing, as shown in FIG. 6. The percentage of mLLDPE was chosen for the y-block. No preprocessing options were used for the y-block. The cross-validation was "leave-out-one" with a maximum of 8 PCs.

Figure 7:
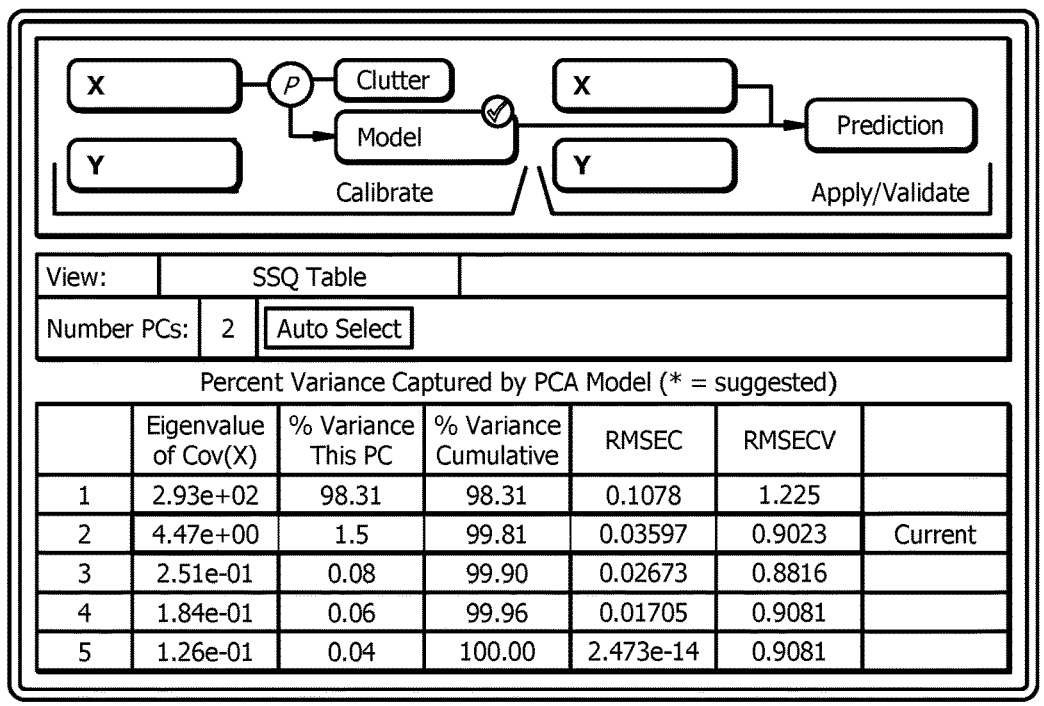
FIG. 7 displays a PCA table in Solo.
Figure 8:
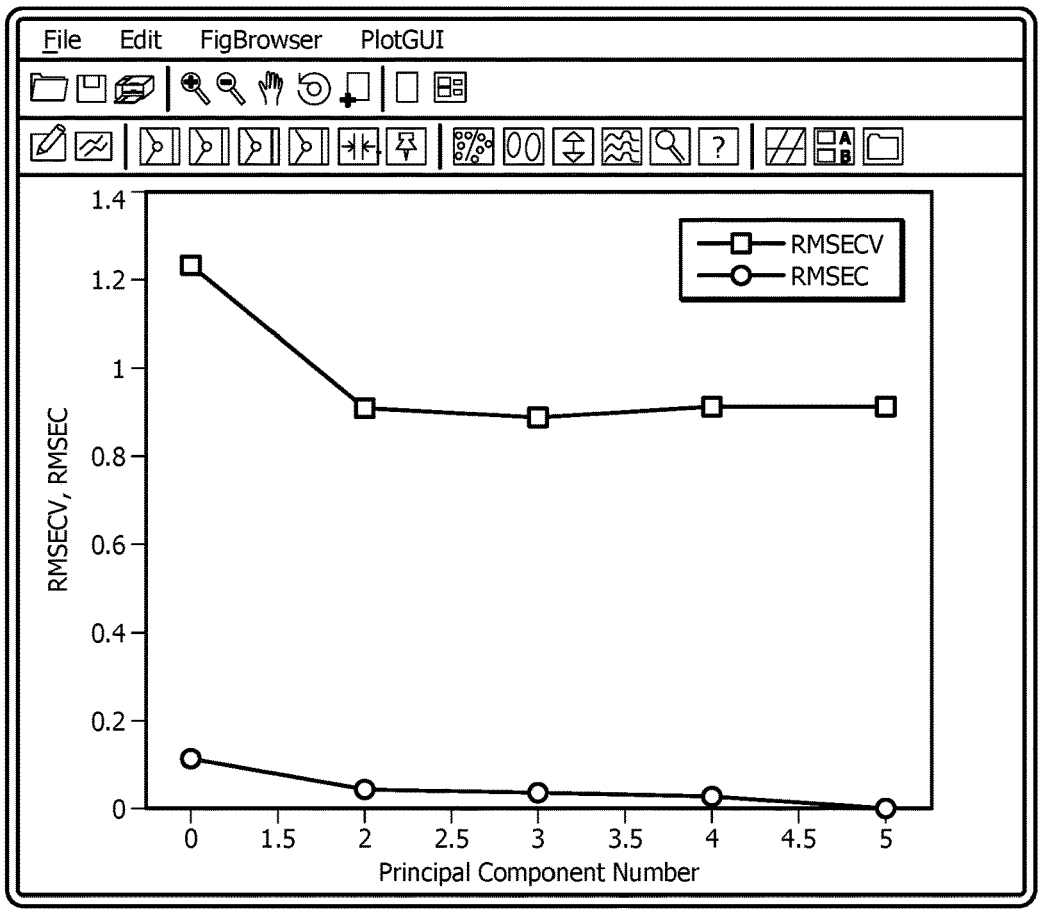
FIG. 8 displays validation and calibration plots in Solo for 2 principle components (PCs)

Modeling showed 98.31% of the data could be modeled from one principle component (PC), as seen from FIGS. 7 and 8. FIG. 8 displays a plot of Root-Mean-Square Error Cross-Validation (RMSECV) and Root-Mean-Square Error of Calibration (RMSEC) vs Principle Component (PC) Number. The RMSECV data in FIG. 8 suggest that using 2 PCs will produce a better model than using 1 PC, although 1 PC could also be used with good modeling results.

Figure 9:
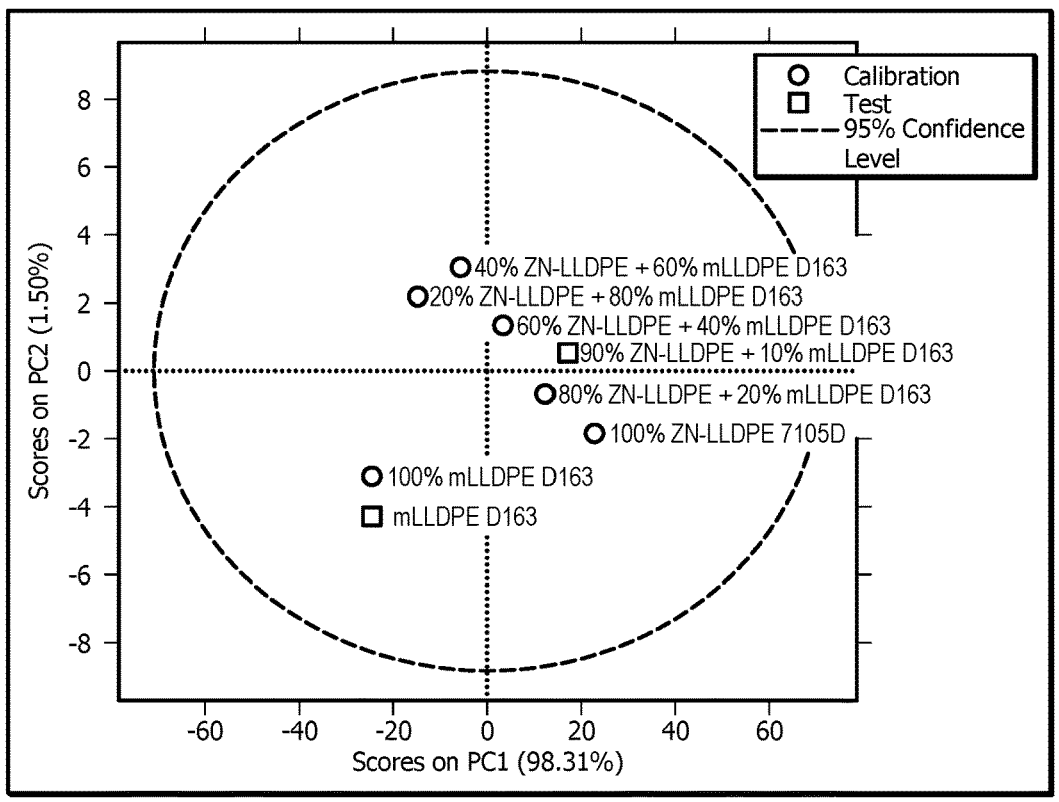
FIG. 9 displays a scores plot showing the calibration and test data.

To check the PCA model, the 90% ZN-LLDPE+10% mLLDPE sample #6 was loaded into the validation blocks along with the aTREF from a pellet sample of the mLLDPE used to make the films. FIG. 9 displays the scores plot showing the test data falls near the calibration samples. The data from the pellet sample of the mLLDPE is labelled with "mLLDPE" in FIG. 9, with no % associated with.

Figure 10:
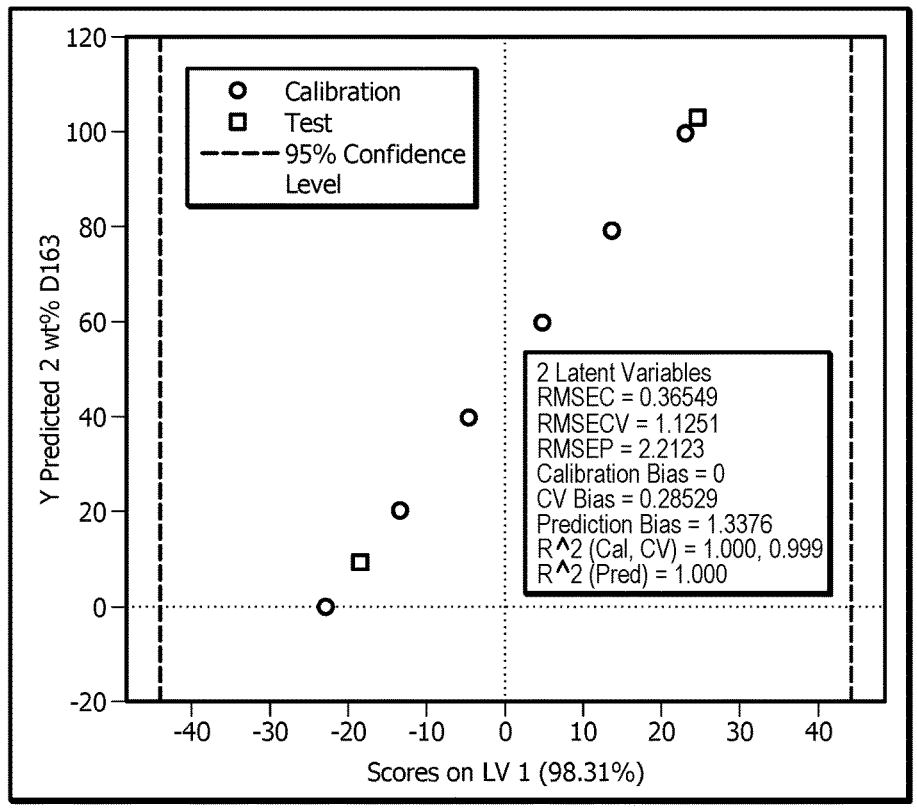
FIG. 10 displays a plot of predicted wt. % of a sample component versus scores for the primary PC.
Figure 11:
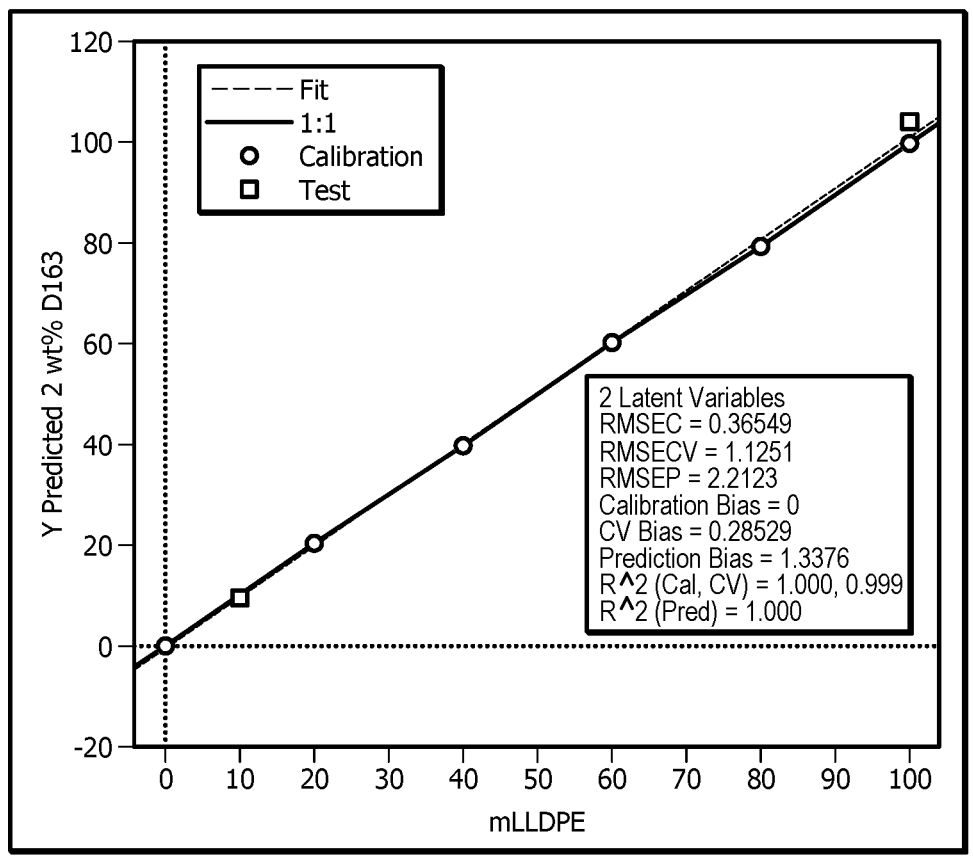
FIG. 11 displays a plot of predicted wt. % of a sample component versus measured value.

After completing the PCA, the data were input in to a PLS regression using the same data sets for the calibration and validation. This time, both the x-block and y-block were mean centered prior to building the model. The result was a linear correlation as shown in FIG. 10, with the scores from the primary PC. FIG. 11 shows the predicted vs. the measured values. The data point for the mLLDPE pellet sits just a little higher on the plot than the data point for the 100% mLLDPE film sample, and the 90% ZN-LLDPE+10% mLLDPE sample #6 is on the linear correlation of the data points. Table 3 displays the Solo data for the PLS model for the predicted values for the samples; wherein the estimated error is also listed in the Table 3, which estimated error is less than 2%. The reproducibility for the aTREF instrument has been established to be 5%, indicating that this estimated error is within the error of the instrument.

TABLE 3

| Sample | Cal/Test Samples | Y Measured wt. % mLLDPE | Y Predicted wt. % mLLDPE | Y Error Estimated wt. % mLLDPE | Y CV Predicted wt. % mLLDPE | Y CV Residual wt. % mLLDPE |
|---|---|---|---|---|---|---|
| 100% mLLDPE | Calibration | 100 | 100.0 | 1.5 | 102.2 | 2.2 |
| 20% ZN-LLDPE + 80% mLLDPE | Calibration | 80 | 79.5 | 1.3 | 79.1 | −0.9 |

TABLE 3-continued

| Sample | Cal/Test Samples | Y Measured wt. % mLLDPE | Y Predicted wt. % mLLDPE | Y Error Estimated wt. % mLLDPE | Y CV Predicted wt. % mLLDPE | Y CV Residual wt. % mLLDPE |
|---|---|---|---|---|---|---|
| 40% ZN-LLDPE + 60% mLLDPE | Calibration | 60 | 60.5 | 1.2 | 60.8 | 0.8 |
| 60% ZN-LLDPE + 40% mLLDPE | Calibration | 40 | 39.9 | 1.2 | 39.8 | −0.2 |
| 80% ZN-LLDPE + 20% mLLDPE | Calibration | 20 | 20.5 | 1.2 | 20.7 | 0.7 |
| 90% ZN-LLDPE + 10% mLLDPE | Test | 10 | 9.6 | 1.3 | N/A | N/A |
| 100% ZN-LLDPE | Calibration | 0 | −0.4 | 1.4 | −0.90 | −0.90 |
| 100% mLLDPE pellet | Test | 100 | 103.1 | 1.7 | N/A | N/A |

Example 4

The ability of aTREF in conjunction with chemometric analysis to account for manufacturing differences between the same type of resin was investigated. Samples #1 and #8 of mLLDPE used in this study generally displayed a "more unimodal" behavior, in the sense that did not produce two distinct bimodal peaks as other similarly manufactured mLLDPE resins would; and this can be observed in FIG. 12, where the aTREF elution trace data is displayed for various mLLDPE samples produced at different times, with substantially similar manufacturing procedures. The mLLDPE samples from Examples 3 and 4 are displayed in FIG. 12 as samples #1 and #8 in accordance with Table 2. Samples #9, #10, and #11 in FIG. 12 are various mLLDPE samples produced at different times. aTREF elution traces for ZN-LLDPE samples produced at different times did not differ as much from each other, as shown in FIG. 13.

Figure 12:
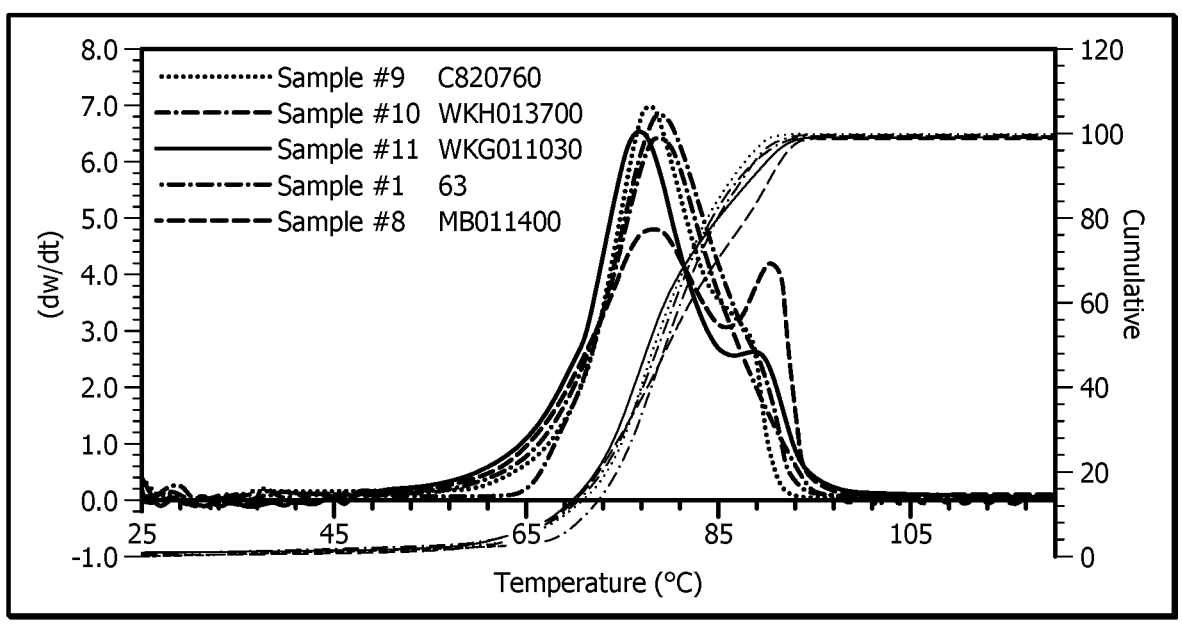
FIG. 12 displays aTREF elution trace data for various mLLDPE samples.
Figure 13:
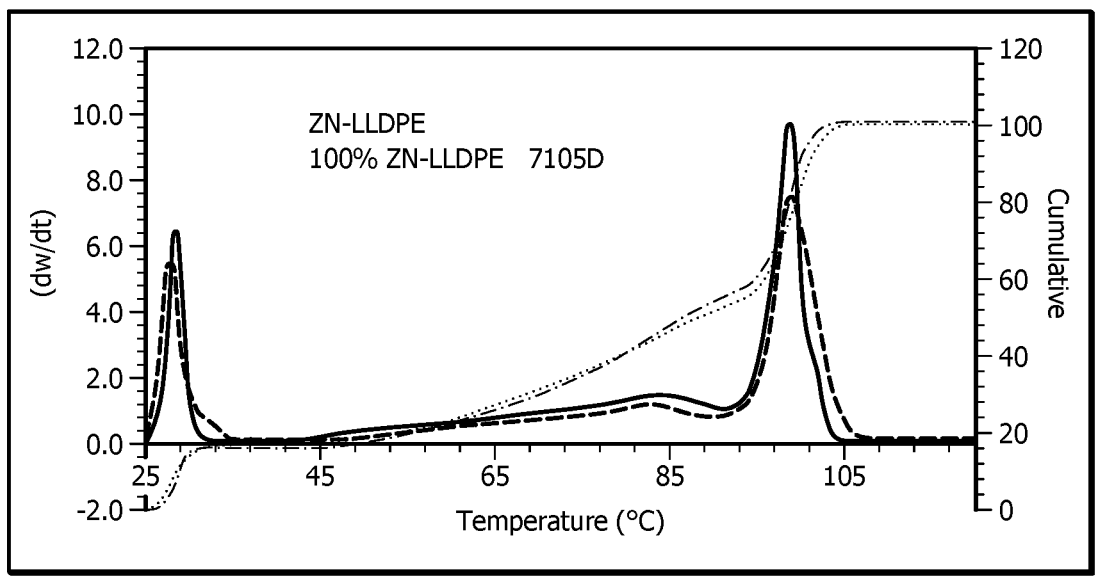
FIG. 13 displays aTREF elution trace data for various ZN-LLDPE samples.
Figure 14:
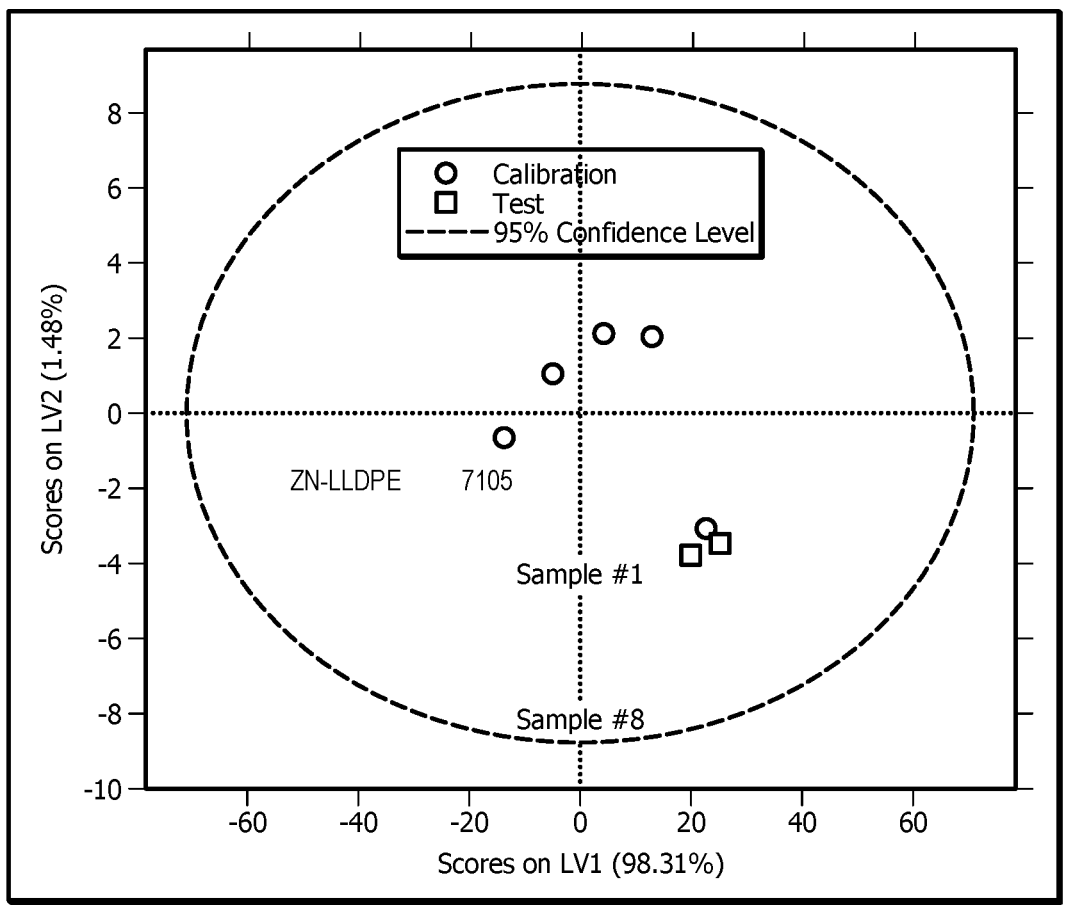
FIG. 14 displays a scores plot for films with various amounts of mLLDPE and ZN-LLDPE.

The data for the samples in FIGS. 12 and 13 was input in the PLS model (as described in Example 3) and sample #11 did not match the results for the other samples. FIG. 14 displays a scores plot showing sample #11 at a significant distance from model samples and other validation samples. The ZN-LLDPE sample and remaining mLLDPE samples (denoted by diamond shaped data point markers in FIG. 14) appeared close to the 100% ZN-LLDPE and 100% mLLDPE data points. The chemometric analysis as disclosed herein was largely able to handle the variation in the mLLDPE samples. However, the pronounced bimodal character of the sample #11 proved to be different enough for the chemometric analysis as disclosed herein to show it as an outlier. As used in FIG. 14 (and FIGS. 16-18), the abbreviation LV represents latent variable when using the PLS model, and corresponds to PC when using the Solo model. "Scores LV" refers to the number principle components, or latent variables, needed to describe the data with regards to the samples. In an aspect, the LV #vs RMSECV can be evaluated to decide how many principle components to use in modeling the data to get the amount of a polymer in the film mixtures.

When looking at the predicted concentration values for the ZN-LLDPE and mLLDPE samples as displayed in Table 4, the chemometric analysis as disclosed herein did relatively well with all but the sample #11. Table 4 displays the predicted wt. % mLLDPE in validation set.

TABLE 4

| Sample # | Y Measured wt. % mLLDPE | Y Predicted wt. % mLLDPE | Y Error Estimated wt. % mLLDPE |
|---|---|---|---|
| 9 | 100 | 97 | 1.6 |
| 10 | 100 | 102 | 1.6 |
| 11 | 100 | 89 | 2.4 |
| 12 | 0 | 2 | 1.4 |

Sample #12 in Table 4 is ZN-LLDPE. Given that sample #11 was relatively different from the other mLLDPE samples, the results in Table 4 were to be expected. The estimated error in the predicted values were all well within the typically accepted 5% experimental error.

Figure 15:
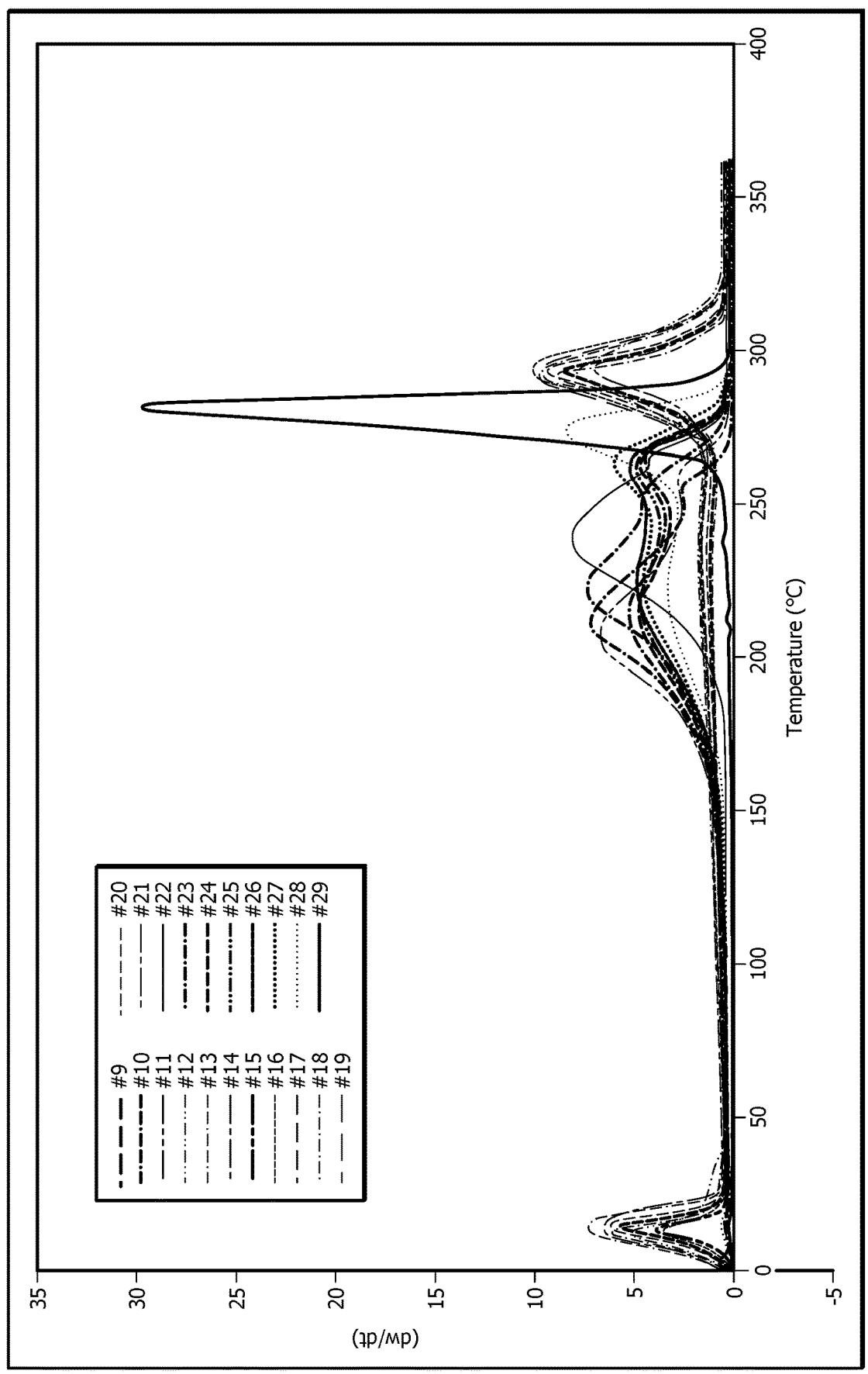
FIG. 15 displays aTREF elution traces for a validation set.

The chemometric analysis as disclosed herein was further tested by adding a few additional ZN-LLDPEs and mLDPEs to the validation set, as seen in Table 5 and FIG. 15.

TABLE 5

| Sample # | Sample Type | Y Measured wt. % mLLDPE | Y Predicted wt. % mLLDPE | Y Error Estimated wt. % mLLDPE |
|---|---|---|---|---|
| 9 | mLLDPE | 100 | 97 | 1.6 |
| 10 | mLLDPE | 100 | 102 | 1.6 |
| 11 | mLLDPE | 100 | 89 | 2.4 |
| 12 | mLLDPE | 0 | 2 | 1.4 |
| 13 | ZN-LLDPE | 0 | 2 | 1.3 |
| 14 | ZN-LLDPE | 0 | 2 | 1.6 |
| 15 | ZN-LLDPE | 0 | −2 | 1.3 |
| 16 | ZN-LLDPE | 0 | −2 | 1.3 |
| 17 | ZN-LLDPE | 0 | −3 | 1.4 |
| 18 | ZN-LLDPE | 0 | −4 | 1.3 |
| 19 | ZN-LLDPE | 0 | −3 | 1.3 |
| 20 | ZN-LLDPE | 0 | −3 | 1.3 |
| 21 | ZN-LLDPE | 0 | 87 | 3.9 |
| 22 | mLLDPE | 0 | 90 | 2.1 |
| 23 | mLLDPE | 0 | 101 | 2.4 |
| 24 | mLLDPE | 0 | 85 | 2.3 |
| 25 | mLLDPE | 0 | 86 | 2.7 |
| 26 | mLLDPE | 0 | 87 | 2.9 |
| 27 | mLLDPE | 0 | 84 | 3.0 |
| 28 | mLLDPE | 0 | 67 | 1.2 |
| 29 | mLLDPE | 0 | 9 | 10.6 |

Samples #13-#20 in Table 5 are various mLLDPE and ZN-LLDPE resins, and samples #21-#29 in Table 5 are various mLLDPE resins. It should be noted that samples #18 and #20 were from the same ZN-LLDPE lot.

Where aTREF data for multiple samples were available for a single resin, all the data was included in the validation set. The ZN-LLDPE samples all had similar aTREF traces, but the mLLDPE resins had aTREF elution traces with relative variety, especially sample #29.

Figure 16:
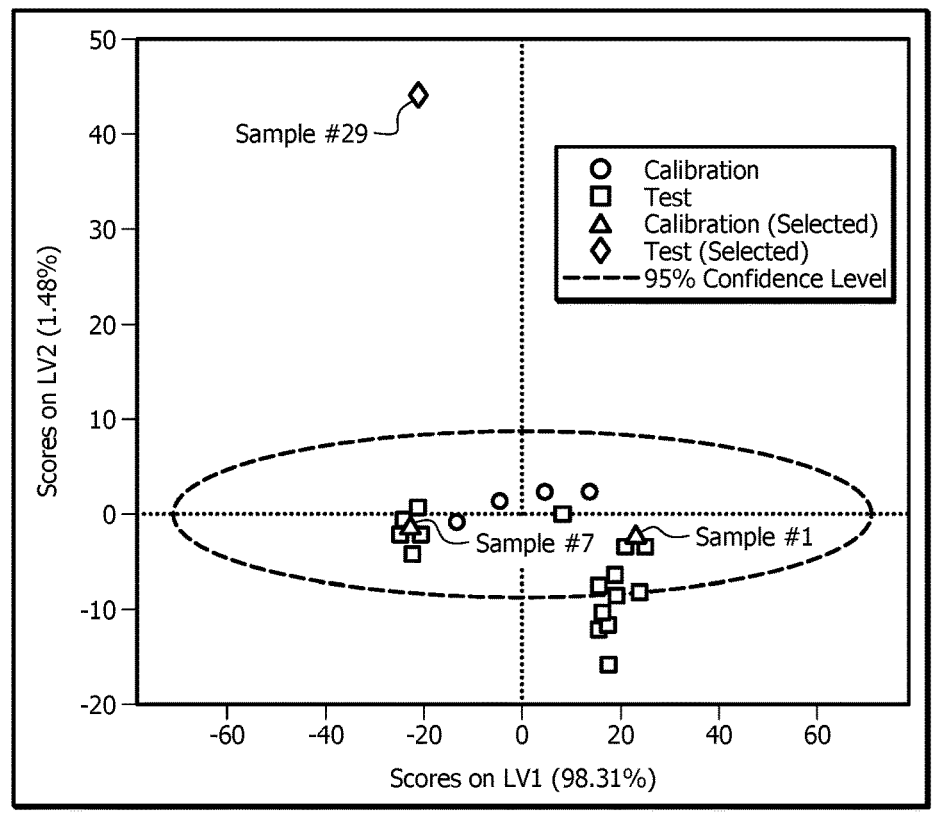
FIG. 16 displays a scores plot showing calibration and validation data sets.
Figure 17:
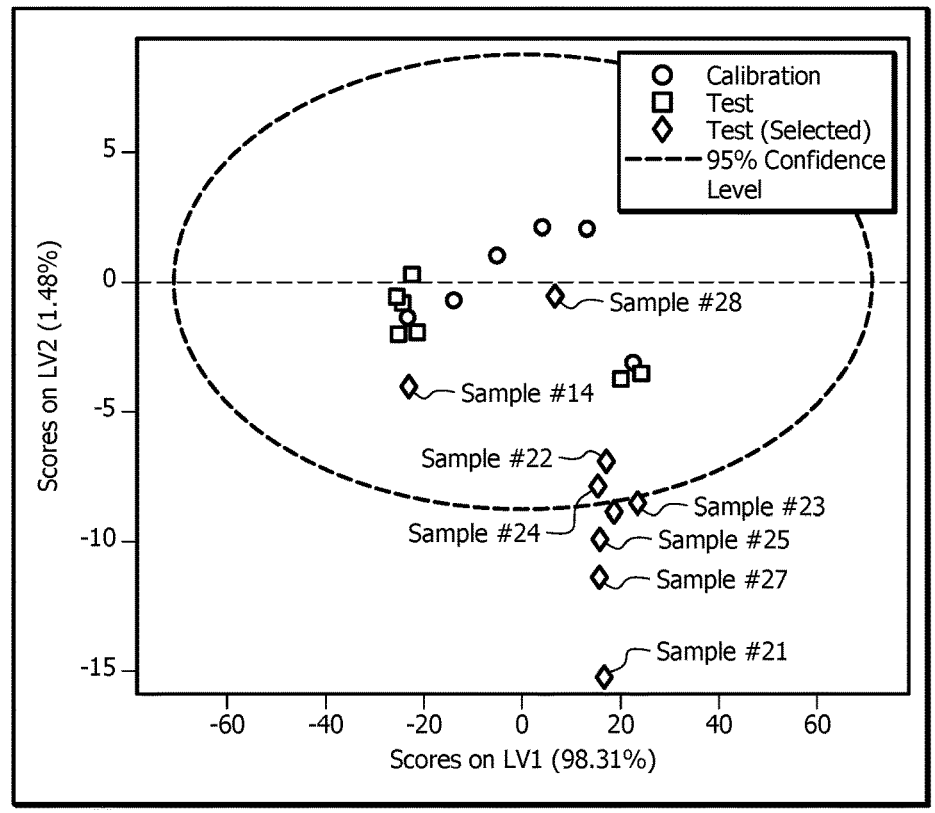
FIG. 17 displays another scores plot showing calibration and validation data sets.

Solo was able to help relatively quickly identify which resins were similar to samples #7 or #1 from Table 2 and which were not, as can be seen in FIG. 16. Sample #29 appears on the scores plot in FIG. 16 relatively far away from the other data points. Given the unique aTREF elution pattern for sample #29, this data point distribution was expected, rendering sample #29 as an outlier. Removing the outlier sample #29 from the graph made it easier to see other resins that stood away from the type of samples similar to samples #7 or #1 from Table 2. Samples #21-18 and #14 were distinct enough in the aTREF to appear at significant distances away from the control resins. Resins #15-#20 showed up relatively close to sample #7. Sample #13 was not as far away from sample #7 as sample #14 and could be identified as a ZN-LLDPE using this model. Even sample #14 appeared in the same quadrant as sample #7. Likewise, samples #21-#28 samples showed up in the same quadrant as the sample #1.

The predicted amounts of mLLDPE in each sample in Table 5 was also investigated in an attempt to see the response of the chemometric analysis as disclosed herein. For the ZN-LLDPE resins, the values were close to zero, as expected. The closer to sample #7 the sample was, the lower the estimated error. Samples #21-#27 all showed values of >80 wt. % and had errors greater than 2%. Sample #28 was calculated to be 67 wt. % with 1.2% error. The prediction for sample #29 was 9 wt. % with 11% error. This was not surprising since the aTREF for sample #29 looks more like sample #7 than sample #1.

Example 5

The ability of aTREF in conjunction with chemometric analysis to account for the presence of various types of polyethylene (PE), such as high density PE (HDPE) was investigated. In order to input the HDPE resin data for analysis in Solo, a variety of the resins were analyzed on aTREF and processed for chemometric analysis, as can be seen in Table 6, which displays a list of additional resins added to the validation set of resins with the predicted wt. % of mLLDPE as generated by PLS model (as described in Example 3).

TABLE 6

| Sample # | Sample Type | Y Measured wt. % mLLDPE | Y Predicted wt. % mLLDPE | Y Error Estimated wt. % mLLDPE |
|---|---|---|---|---|
| 30 | mLLDPE | 0 | −72 | 2.3 |
| 31 | mLLDPE | 0 | 103 | 1.4 |
| 32 | mLLDPE | 0 | 93 | 2.1 |
| 33 | mLLDPE | 0 | 100 | 1.4 |
| 34 | mLLDPE | 0 | 96 | 2.0 |
| 35 | mLLDPE | 0 | 97 | 1.6 |
| 36 | mLLDPE | 0 | 91 | 1.5 |
| 37 | HDPE | 0 | −30 | 1.6 |
| 38 | HDPE | 0 | −16 | 3.0 |
| 39 | MDPE | 0 | 5 | 3.0 |
| 40 | ZN-HDPE | 0 | −4 | 1.4 |
| 41 | ZN-HDPE | 0 | −5 | 1.4 |
| 42 | HDPE | 0 | −17 | 2.7 |
| 43 | HDPE | 0 | −31 | 2.0 |
| 44 | HDPE | 0 | −27 | 2.3 |
| 45 | HDPE | 0 | −35 | 1.8 |
| 46 | HDPE | 0 | −27 | 2.2 |
| 47 | HDPE | 0 | −12 | 2.9 |
| 48 | HDPE | 0 | −27 | 1.8 |

TABLE 6-continued

| Sample # | Sample Type | Y Measured wt. % mLLDPE | Y Predicted wt. % mLLDPE | Y Error Estimated wt. % mLLDPE |
|---|---|---|---|---|
| 49 | HDPE | 0 | −42 | 1.8 |
| 50 | HDPE | 0 | −37 | 1.7 |
| 51 | HDPE | 0 | −38 | 3.0 |
| 52 | HDPE | 0 | −33 | 2.1 |
| 53 | HDPE | 0 | −18 | 2.8 |
| 54 | ZN-HDPE | 0 | −10 | 1.4 |
| 55 | ZN-HDPE | 0 | −22 | 1.7 |
| 56 | ZN-HDPE | 0 | −18 | 1.5 |
| 57 | ZN-HDPE | 0 | −10 | 1.4 |
| 58 | ZN-HDPE | 0 | −4 | 1.4 |
| 59 | ZN-HDPE | 0 | −14 | 2.5 |
| 60 | ZN-HDPE | 0 | −2 | 2.7 |
| 61 | ZN-HDPE | 0 | −4 | 2.7 |
| 62 | HDPE | 0 | −3 | 3.0 |
| 63 | HDPE | 0 | −19 | 1.5 |
| 64 | HDPE | 0 | −18 | 1.6 |
| 65 | HDPE | 0 | −33 | 2.1 |
| 66 | HDPE | 0 | −5 | 6.3 |
| 67 | ZN-HDPE | 0 | −12 | 1.6 |
| 68 | LDPE | 0 | 102 | 1.4 |
| 69 | LDPE | 0 | 101 | 1.5 |
| 70 | LDPE | 0 | 101 | 1.5 |
| 71 | LDPE | 0 | 110 | 1.5 |
| 72 | LDPE | 0 | 97 | 1.9 |
| 73 | LDPE | 0 | 97 | 2.0 |
| 74 | LDPE | 0 | 84 | 1.3 |
| 75 | LDPE | 0 | 115 | 1.7 |
| 76 | LDPE | 0 | 95 | 1.4 |
| 77 | ZN-MDPE | 0 | −7 | 1.4 |
| 78 | MDPE | 0 | −3 | 3.8 |
| 79 | MDPE | 0 | 3 | 2.5 |

In Table 6, samples #30-#36 are mLLDPE; samples #37-#67 are HDPE; samples #68-#76 are LDPE; and samples #77-#79 are MDPE. It should be noted that sample #35 in Table 6 is the same as sample #9 in Table 5. For the resins in Table 6, the HDPE samples denoted as ZN-HDPE were produced with a ZN catalyst, while the rest of the HDPE samples were produced with a Cr-based catalyst. However, no distinction was made between HDPE and ZN-HDPE in the analysis. For the resins in Table 6, the MDPE samples denoted as ZN-MDPE were produced with a ZN catalyst, while the rest of the MDPE samples were produced with a Cr-based catalyst. However, no distinction was made between MDPE and ZN-MDPE in the analysis.

Figure 18:
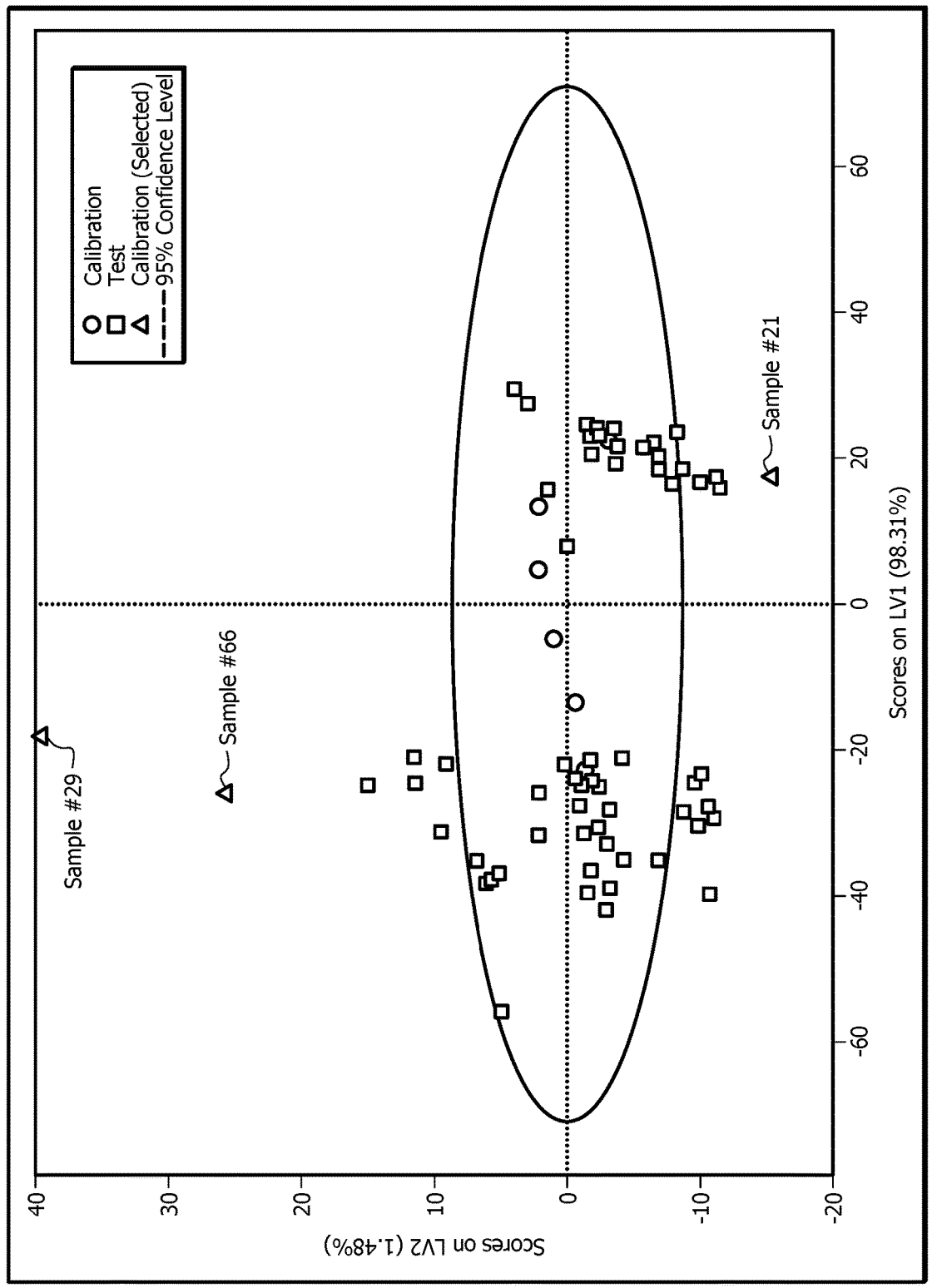
FIG. 18 displays a scores plot with different types of high density polyethylene (HDPE), low density polyethylene (LDPE), ZN-LLDPE, and mLLDPE.

The data were then inputted into the chemometric analysis model, as seen in Table 6 and FIG. 18. As shown in FIG. 18, the data are scattered across the left-right quadrants according to density, higher densities to the left and lower densities to the right. The division between the upper and lower quadrants involved more than just the density of the resin. Catalyst type appears to have played a part in the distribution.

Example 6

The ability of aTREF to resolve (e.g., identify and quantify the different polymer components) between mLLDPE and HDPE was investigated. A tri-layer film was made from two layers of mLLDPE similar to sample #29 from Table 5 (30%) and a single layer of HDPE having a density of 0.962 g/cc (70%), wherein film samples were analyzed by aTREF and chemometric analysis as described in Examples 2 and 3. The aTREF analysis showed the film contained no separate (e.g., distinct) mLLDPE and HDPE peaks. A calibration set of resins was established by using aTREF data from 80 commercial lots of PE: 31 HDPE, 11 LDPE, 11 ZN-LLDPE, 4 MDPE, and 23 mLLDPE. The aTREF data from the film was used as the validation set. The aTREF analysis showed the film contained no LDPE. These resins were eliminated from the analysis. The refined chemometric analysis showed the film shared more characteristics with resins with a density of 0.943-0.957 g/cm$^3$. The data from this analysis showed that there may be some combinations of PE that are more difficult than others to be characterized by the methods disclosed herein. While the data for this film sample does not fall relatively close to either mLLDPE or HDPE, the analysis data for this film sample does fall close to the density such a blend would likely create. The two resins (mLLDPE and HDPE) co-crystallized so the characteristic aTREF signals for the parent resins were obscured to some extent. However, there were some features of each of the mLLDPE and HDPE resins that were observable, such as the small soluble fraction (characteristic of both Cr-HDPE and mLL-DPEs). LLDPE resins have a large soluble fraction typically, the fronting at the start of the main elution peak (seen in LLDPE and some mLLDPE). The high temperature shoulder was mostly seen with HDPE (either chrome or ZN).

Example 7

The ability of aTREF to resolve (e.g., identify and quantify the different polymer components) between different types of PE, such as HDPE, LDPE, ZN-LLDPE, plastomers, and mLLDPE was investigated. Eleven 5-layer films made using 2 different types of mLLDPE, 1 type of HDPE, 1 type of ZN-LLDPE, 1 type of LDPE, 1 type of polyolefin plastomer. The films were subjected to aTREF analysis and chemometric analysis as described in Examples 2 and 3. The calibration set of resins was established by using the aTREF data from 80 commercial lots of PE: 31 HDPE, 11 LDPE, 11 ZN-LLDPE, 4 MDPE, and 23 mLLDPE. The validation set was comprised of the eleven film samples. A PCA model was able to put the film samples on a graph in areas that gave strong indications of which resins were in the sample and closest to the resin in the highest concentration. These data could then be used to direct the samples to the PLS model needed to quantify the amounts of each type of resin in the sample. These data were introduced to two binary models (both were ZN-LLDPE/mLLDPE models), and Solo did a relatively good job of estimating the amount of mLLDPE in 3 of 7 samples that contained mLLDPE. Solo also predicted the relatively high amount of mLLDPE in samples with a different type of mLLDPE. The PLS model was run for LDPE-mLLDPE blends having the same LDPE, but different types of mLLDPEs. The results showed the mLLDPE predictions were relatively good for films that contained mLLDPE. The predictions of the amount of LDPE were relatively closer for the film samples.

Example 8

The ability of aTREF analysis in conjunction with chemometric analysis as disclosed herein could be used to resolve (e.g., identify and quantify the different polymer components) between different types of PE, such as LDPE and LLDPE, for example LDPE and LLDPE used in films as described in U.S. Pat. No. 7,678,468, which is incorporated by reference herein in its entirety. The films (e.g., film samples) could be subjected to aTREF analysis and chemometric analysis as described in Examples 2 and 3. The calibration set of resins could be established by using the aTREF data from various PE resins, such as commercial lots of PE: LDPE samples and LLDPE samples. The validation set would be comprised of the film samples. A PCA model would be able to put the film samples on a graph in areas that would give strong indications of which resins were in the sample and closest to the resin in the highest concentration.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

ADDITIONAL DISCLOSURE

The following enumerated embodiments are provided as nonlimiting examples.

A first aspect, which is a method of analyzing a polymer resin comprising (a) providing a polymer sample of the polymer resin, wherein the polymer sample comprises two or more polymer components; (b) subjecting at least a portion of the polymer sample to analytical temperature rising elution fractionation (aTREF) analysis to yield an aTREF elution trace, wherein the subjecting comprises: (i) contacting at least a portion of the polymer sample with an aTREF solvent to form a polymer sample solution; (ii) introducing at least a portion of the polymer sample solution into an aTREF column and allowing the polymer sample solution to elute along the aTREF column, wherein the two or more polymer components elute at different elution rates along the aTREF column; (iii) eluting an aTREF eluent from the aTREF column, wherein the aTREF eluent comprises the two or more polymer components eluting at the different elution rates from the aTREF column; and (iv) subjecting at least a portion of the aTREF eluent to infrared (IR) detection to yield the aTREF elution trace; (c) identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; and (d) quantifying an amount of each of the two or more identified polymer components in the polymer sample to yield two or more quantified polymer components, wherein the quantifying comprises chemometric analysis of the aTREF elution trace.

A second aspect, which is the method of the first aspect, wherein the step (ii) of introducing at least a portion of the polymer sample solution into an aTREF column and allowing the polymer sample solution to elute along the aTREF column comprises (1) at least a portion of the polymer in the polymer sample solution crystallizing out of the solution onto the aTREF column under substantially static conditions to yield a column-crystallized polymer; and (2) at least a portion of the column-crystallized polymer re-dissolving back into solution under flow conditions and eluting off the aTREF column with increasing a temperature in the aTREF column.

A third aspect, which is the method of any one of the first and the second aspects, wherein the aTREF analysis is performed on an analytical instrument selected from the group consisting of an aTREF instrument, a crystallization elution fractionation (CEF) instrument, a crystallization analysis fractionation (CRYSTAF)-aTREF instrument, an aTREF-gel permeation chromatography (GPC) instrument, and combinations thereof; wherein the analytical instrument comprises the aTREF column.

A fourth aspect, which is the method of any one of the first through the third aspects, wherein the chemometric analysis comprises pre-processing the aTREF elution trace to yield a pre-processed aTREF elution trace, wherein the pre-processing comprises baseline correction, mean centering (MC), normalization (N), baseline correction and MC, normalization and MC, or combinations thereof.

A fifth aspect, which is the method of the fourth aspect, wherein the pre-processed aTREF elution trace is subjected to principal components analysis (PCA) followed by partial least squares (PLS) regression analysis to predict the amount of each of the two or more polymer components in the polymer sample, thereby quantifying the amount of each of the two or more identified polymer components in the polymer sample.

A sixth aspect, which is the method of the fifth aspect, wherein PCA further comprises root mean square (RMS) analysis to determine a number of principal components (PCs) necessary to predict the amount of each of the two or more polymer components in the polymer sample; and wherein the number of PCs is an integer equal to or greater than 1.

A seventh aspect, which is the method of the sixth aspect, wherein the RMS analysis comprises root mean square error of cross validation (RMSECV) analysis.

An eighth aspect, which is the method of any one of the first through the seventh aspects, wherein the chemometric analysis further comprises employing a calibration set that comprises calibration data for known polymer resins having a known amount of each of the two or more identified polymer components.

A ninth aspect, which is the method of any one of the first through the eighth aspects, wherein the polymer resin comprises a semi-crystalline polymer, a polyethylene resin, a polypropylene resin, an ethylene-propylene copolymer, an isotactic polypropylene, a syndiotactic polypropylene, a syndiotactic polystyrene, or combinations thereof.

A tenth aspect, which is the method of any one of the first through the ninth aspects, wherein the two or more polymer components comprise a metallocene-catalyzed resin, a Ziegler-Natta (ZN)-catalyzed resin, a chromium-catalyzed resin, a non-metallocene single-site-catalyzed resin, a cross-linked resin, a peroxide-treated resin, low density polyethylene (LDPE), linear low density polyethylene (LLDPE), metallocene-catalyzed linear low density polyethylene (mLLDPE), peroxide-treated linear low density polyethylene (pLLDPE), peroxide-treated metallocene-catalyzed linear low density polyethylene (pmLLDPE), ZN-catalyzed LLDPE, chromium-catalyzed LLDPE, non-metallocene single-site-catalyzed LLDPE, medium density polyethylene (MDPE), metallocene-catalyzed medium density polyethylene (mMDPE), high density polyethylene (HDPE), a plastomer, an elastomer, or combinations thereof.

An eleventh aspect, which is the method of any one of the first through the tenth aspects, wherein the step (c) of identifying the two or more polymer components of the polymer sample accounts for the type of catalyst used for producing the two or more polymer components.

A twelfth aspect, which is the method of any one of the first through the eleventh aspects, wherein the two or more polymer components comprise Ziegler-Natta-catalyzed linear low density polyethylene (ZN-LLDPE) and metallocene-catalyzed linear low density polyethylene (mLLDPE).

A thirteenth aspect, which is the method of any one of the first through the twelfth aspects, wherein the polymer resin is a polymer film, a multi-layer polymer film, a polymer blend, a unimodal polymer, a multimodal polymer, a bimodal polymer, a trimodal polymer, a terpolymer, or combinations thereof.

A fourteenth aspect, which is the method of any one of the first through the thirteenth aspects, wherein the aTREF solvent comprises a halogenated aromatic hydrocarbon solvent, 1,2,4-trichlorobenzene (TCB), ortho-dichlorobenzene (o-DCB), or combinations thereof.

A fifteenth aspect, which is the method of any one of the first through the fourteenth aspects further comprising using a supplemental analytical technique to additionally characterize the polymer resin, wherein the supplemental analytical technique comprises crystallization analysis fractionation (CRYSTAF), optical microscopy, atomic force microscopy (AFM), IR spectroscopy, Raman spectroscopy, inductively coupled plasma (ICP) analysis, thermal gradient interaction chromatography (TGIC), thermomechanical analysis (TMA), differential scanning calorimetry (DSC), nuclear magnetic resonance (NMR) spectroscopy, gel permeation chromatography (GPC), or combinations thereof.

A sixteenth aspect, which is a method of producing a polymer resin comprising (a) providing a polymer sample of the polymer resin, wherein the polymer sample comprises two or more polymer components; (b) subjecting at least a portion of the polymer sample to analytical temperature rising elution fractionation (aTREF) analysis to yield an aTREF elution trace; (c) identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; (d) quantifying an amount of each of the two or more identified polymer components in the polymer sample to yield two or more quantified polymer components, wherein the quantifying comprises chemometric analysis of the aTREF elution trace; and (e) producing the polymer resin by: (i) responsive to step (c), selecting one or more monomers that can form the two or more identified polymer components; and polymerizing the one or more monomers to produce the polymer resin; wherein the polymerizing occurs under a plurality of polymerization conditions; and wherein each polymerization condition of the plurality of polymerization conditions is selected responsive to step (d) from the group consisting of monomer concentration, comonomer concentration, hydrogen to monomer ratio, temperature, catalyst concentration, cocatalyst concentration, pressure, residence time, reactor solids concentration, and combinations thereof; (ii) responsive to step (c), selecting the two or more polymer components; and responsive to step (d), blending the two or more polymer components to produce the polymer resin; or (iii) both (i) and (ii).

A seventeenth aspect, which is the method of the sixteenth aspect further comprising forming the polymer resin produced in step (e) into an article.

An eighteenth aspect, which is the method of the seventeenth aspect, wherein the article comprises a film, a multilayer film, a pipe, a container, a bottle, a drum, an utensil, a toy, a membrane, a geomembrane, a liner, or combinations thereof; wherein the multilayer film comprises two or more layers, and wherein the two or more layers can comprise the same resin or different resins.

A nineteenth aspect, which is the method of any one of the sixteenth through the eighteenth aspects, wherein the polymer resin is a multimodal polyethylene resin.

A twentieth aspect, which a system for analyzing a polyethylene resin comprising an analytical instrument comprising an analytical temperature rising elution fractionation (aTREF) column and an infrared (IR) detector; wherein the aTREF column is configured to receive a polyethylene sample solution, wherein the polyethylene sample solution comprises a polyethylene sample of the polyethylene resin and an aTREF solvent, wherein the polyethylene sample comprises two or more polyethylene components; wherein the aTREF column is configured to elute the two or more polyethylene components at different elution rates along the aTREF column to produce an aTREF eluent; and wherein the IR detector is configured to detect the two or more polyethylene components in the aTREF eluent and yield an aTREF elution trace; and a computer system configured to receive the aTREF elution trace from the analytical instrument, wherein the computer system comprises at least one processor; wherein the at least one processor compares the aTREF elution trace with an identification library and identifies the two or more polyethylene components of the polyethylene sample to yield two or more identified polyethylene components; wherein the identification library comprises a plurality of known polyethylene aTREF elution traces, wherein each of the plurality of known polyethylene aTREF elution traces is correlated with a known polyethylene component, wherein the known polyethylene component is characterized by an identifying parameter, and wherein the identifying parameter is selected from the group consisting of density, short chain branching, crystallization temperature, melt index, high load melt index, molecular weight distribution, and combinations thereof; and wherein the at least one processor performs chemometric analysis of the aTREF elution trace to quantify an amount of each of the two or more identified polyethylene components in the polyethylene sample to yield two or more quantified polyethylene components.

A twenty-first aspect, which is the system of the twentieth aspect, wherein the analytical instrument comprises an aTREF instrument, a crystallization elution fractionation (CEF) instrument, a crystallization analysis fractionation (CRYSTAF)-aTREF instrument, an aTREF-gel permeation chromatography (GPC) instrument, or combinations thereof.

A twenty-second aspect, which is the system of the twenty-first aspect, wherein the CEF instrument further comprises a capillary viscometer detector configured to provide data on composition-molar mass interdependence of the two or more polyethylene components.

A twenty-third aspect, which is the system of the twentieth through the twenty-second aspects further comprising a recycling system, wherein the recycling system is configured to receive the polyethylene resin.

A twenty-fourth aspect, which is the system of the twenty-third aspect, wherein the recycling system comprises a shaping system configured to form at least a portion of the polyethylene resin into a shaped article.

A twenty-fifth aspect, which is the system of the twentieth through the twenty-fourth aspects, wherein the recycling system is configured to feed at least a portion of the polyethylene resin to a pyrolysis unit, a gasification unit, a combustion unit, or combinations thereof.

A twenty-sixth aspect, which is the system of the twentieth through the twenty-fifth aspects, wherein the recycling system is configured to separate the two or more quantified polyethylene components from the polyethylene resin to yield two or more separated polyethylene components; and wherein at least a portion of the separated polyethylene components are used for forming an article, as a feedstock to a pyrolysis unit, a gasification unit, a combustion unit, or combinations thereof, or both for forming an article and as a feedstock to a pyrolysis unit, a gasification unit, a combustion unit, or combinations thereof.

A twenty-seventh aspect, which is the system of the twentieth through the twenty-sixth aspects further comprising a polymerization reactor, wherein the polymerization reactor is configured to polymerize ethylene to produce the polyethylene resin; wherein the reactor operates under a plurality of polymerization conditions comprising monomer concentration, comonomer concentration, hydrogen to monomer ratio, temperature, catalyst concentration, cocatalyst concentration, pressure, residence time, reactor solids concentration, or combinations thereof; and a control system configured to receive the amount of each of the two or more identified polyethylene components in the polyethylene sample from the computer system, wherein the control system comprises at least one controller; and wherein the at least one controller adjusts at least one of the plurality of polymerization conditions.

A twenty-eighth aspect, which is the system of the twenty-seventh aspect further comprising a shaping system configured to receive the polyethylene resin from the polymerization reactor, wherein the shaping system is configured to form at least a portion of the polyethylene resin into a shaped article.

A twenty-ninth aspect, which is the system of any one of the twenty-seventh an the twenty-eighth aspects, wherein the polymerization reactor is selected from the group consisting of a loop slurry reactor, a fluidized bed gas phase reactor, a solution reactor, a continuous stirred-tank reactor (CSTR), an autoclave, a tubular reactor, a multi-zone circulating reactor (MZCR), and combinations thereof.

A thirtieth aspect, which is a method of recycling a polymer resin comprising (a) providing a polymer sample of the polymer resin, wherein the polymer sample comprises two or more polymer components; (b) subjecting at least a portion of the polymer sample to analytical temperature rising elution fractionation (aTREF) analysis to yield an aTREF elution trace; (c) identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; (d) quantifying an amount of each of the two or more identified polymer components in the polymer sample to yield two or more quantified polymer components, wherein the quantifying comprises chemometric analysis of the aTREF elution trace; and (e) recycling at least a portion of the polymer resin having two or more quantified polymer components.

A thirty-first aspect, which is the method of the thirtieth aspect, wherein the step (e) of recycling comprises (i) separating the two or more quantified polymer components from the polymer resin to yield two or more separated polymer components, (ii) forming at least a portion of the polymer resin, at least a portion of the two or more separated polymer components, or both at least a portion of the polymer resin and at least a portion of the two or more separated polymer components into an article, (iii) using at least a portion of the polymer resin, at least a portion of the two or more separated polymer components, or both at least a portion of the polymer resin and at least a portion of the two or more separated polymer components as a pyrolysis feedstock, gasification feedstock, combustion feedstock, or combinations thereof, or (iv) any combination of (i)-(iii).

A thirty-second aspect, which is the method of any one of the thirtieth and the thirty-first aspects, wherein the polymer resin is a polyethylene resin.

A thirty-third aspect, which is the method of the thirty-second aspect, wherein the polyethylene resin is a multimodal polyethylene resin.

A thirty-fourth aspect, which is the method of any one of the thirtieth through the thirty-third aspects, wherein the chemometric analysis comprises pre-processing the aTREF elution trace to yield a pre-processed aTREF elution trace, wherein the pre-processing comprises baseline correction, mean centering (MC), normalization (N), baseline correction and MC, normalization and MC, or combinations thereof; wherein the pre-processed aTREF elution trace is subjected to principal components analysis (PCA) followed by partial least squares (PLS) regression analysis to predict the amount of each of the two or more polymer components in the polymer sample, thereby quantifying the amount of each of the two or more identified polymer components in the polymer sample; and wherein PCA further comprises root mean square error of cross validation (RMSECV) analysis to determine a number of principal components (PCs) necessary to predict the amount of each of the two or more polymer components in the polymer sample; and wherein the number of PCs is an integer equal to or greater than 1.

A thirty-fifth aspect, which is a method of recycling a polymer resin comprising (a) providing a polymer sample of the polymer resin, wherein the polymer sample comprises two or more polymer components; (b) subjecting at least a portion of the polymer sample to Fourier-transform infrared (FTIR) spectroscopy to yield an FTIR spectrum; (c) identifying the two or more polymer components of the polymer sample to yield two or more identified polymer components; wherein the identifying comprises comparing the FTIR spectrum with an identification library that comprises a plurality of known polymer FTIR spectra, wherein each of the plurality of known polymer FTIR spectra is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; (d) quantifying an amount of each of the two or more identified polymer components in the polymer sample to yield two or more quantified polymer components, wherein the quantifying comprises chemometric analysis of the FTIR spectrum; and (e) recycling at least a portion of the polymer resin having two or more quantified polymer components.

A thirty-sixth aspect, which is the method of the thirty-fifth aspect, wherein the step (e) of recycling comprises (i) separating the two or more quantified polymer components from the polymer resin to yield two or more separated polymer components, (ii) forming at least a portion of the polymer resin, at least a portion of the two or more separated polymer components, or both at least a portion of the polymer resin and at least a portion of the two or more separated polymer components into an article, (iii) using at least a portion of the polymer resin, at least a portion of the two or more separated polymer components, or both at least a portion of the polymer resin and at least a portion of the two or more separated polymer components as a pyrolysis feedstock, gasification feedstock, combustion feedstock, or combinations thereof, or (iv) any combination of (i)-(iii).

A thirty-seventh aspect, which is the method of anyone of the thirty-fifth and the thirty-sixth aspects, wherein the polymer resin is a polyethylene resin.

A thirty-eighth aspect, which is the method of the thirty-seventh aspect, wherein the polyethylene resin is a multimodal polyethylene resin.

A thirty-ninth aspect, which is the method of any one of the thirty-fifth through the thirty-eighth aspects, wherein the chemometric analysis comprises pre-processing the FTIR spectrum to yield a pre-processed FTIR spectrum, wherein the pre-processing comprises baseline correction, mean centering (MC), normalization (N), baseline correction and MC, normalization and MC, or combinations thereof; wherein the pre-processed FTIR spectrum is subjected to principal components analysis (PCA) followed by partial least squares (PLS) regression analysis to predict the amount of each of the two or more polymer components in the polymer sample, thereby quantifying the amount of each of the two or more identified polymer components in the polymer sample; and wherein PCA further comprises root mean square error of cross validation (RMSECV) analysis to determine a number of principal components (PCs) necessary to predict the amount of each of the two or more polymer components in the polymer sample; and wherein the number of PCs is an integer equal to or greater than 1.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, and the like; greater than 0.10 includes 0.11, 0.12, 0.13, and the like). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method of analyzing a polymer resin comprising:
   (a) providing a polymer sample of the polymer resin, wherein the polymer sample comprises two or more polymer components;
   (b) subjecting at least a portion of the polymer sample to analytical temperature rising elution fractionation (aTREF) analysis to yield an aTREF elution trace, wherein the subjecting comprises:
      (i) contacting at least a portion of the polymer sample with an aTREF solvent to form a polymer sample solution;
      (ii) introducing at least a portion of the polymer sample solution into an aTREF column and allowing the polymer sample solution to elute along the aTREF column, wherein the two or more polymer components elute at different elution rates along the aTREF column;
      (iii) eluting an aTREF eluent from the aTREF column, wherein the aTREF eluent comprises the two or more polymer components eluting at the different elution rates from the aTREF column; and
      (iv) subjecting at least a portion of the aTREF eluent to infrared (IR) detection to yield the aTREF elution trace;
   (c) identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof; and
   (d) quantifying an amount of each of the two or more identified polymer components in the polymer sample to yield two or more quantified polymer components, wherein the quantifying comprises chemometric analysis of the aTREF elution trace.

2. The method of claim 1, wherein the step (ii) of introducing at least a portion of the polymer sample solution into an aTREF column and allowing the polymer sample solution to elute along the aTREF column comprises (1) at least a portion of the polymer in the polymer sample solution crystallizing out of the solution onto the aTREF column under substantially static conditions to yield a column-crystallized polymer; and (2) at least a portion of the column-crystallized polymer re-dissolving back into solution under flow conditions and eluting off the aTREF column with increasing a temperature in the aTREF column.

3. The method of claim 1, wherein the aTREF analysis is performed on an analytical instrument selected from the group consisting of an aTREF instrument, a crystallization elution fractionation (CEF) instrument, a crystallization analysis fractionation (CRYSTAF)-aTREF instrument, an aTREF-gel permeation chromatography (GPC) instrument, and combinations thereof; wherein the analytical instrument comprises the aTREF column.

4. The method of claim 1, wherein the chemometric analysis comprises pre-processing the aTREF elution trace to yield a pre-processed aTREF elution trace, wherein the pre-processing comprises baseline correction, mean centering (MC), normalization (N), baseline correction and MC, normalization and MC, or combinations thereof.

5. The method of claim 4, wherein the pre-processed aTREF elution trace is subjected to principal components analysis (PCA) followed by partial least squares (PLS) regression analysis to predict the amount of each of the two or more polymer components in the polymer sample, thereby quantifying the amount of each of the two or more identified polymer components in the polymer sample.

6. The method of claim 5, wherein PCA further comprises root mean square (RMS) analysis to determine a number of principal components (PCs) necessary to predict the amount of each of the two or more polymer components in the polymer sample; and wherein the number of PCs is an integer equal to or greater than 1.

7. The method of claim 1, wherein the chemometric analysis further comprises employing a calibration set that comprises calibration data for known polymer resins having a known amount of each of the two or more identified polymer components.

8. The method of claim 1, wherein the polymer resin comprises a semi-crystalline polymer, a polyethylene resin, a polypropylene resin, an ethylene-propylene copolymer, an isotactic polypropylene, a syndiotactic polypropylene, a syndiotactic polystyrene, or combinations thereof.

9. The method of claim 1, wherein the two or more polymer components comprise a metallocene-catalyzed resin, a Ziegler-Natta (ZN)-catalyzed resin, a chromium-catalyzed resin, a non-metallocene single-site-catalyzed resin, a crosslinked resin, a peroxide-treated resin, low density polyethylene (LDPE), linear low density polyethylene (LLDPE), metallocene-catalyzed linear low density polyethylene (mLLDPE), peroxide-treated linear low density polyethylene (pLLDPE), peroxide-treated metallocene-catalyzed linear low density polyethylene (pmLLDPE), ZN-catalyzed LLDPE, chromium-catalyzed LLDPE, non-metallocene single-site-catalyzed LLDPE, medium density polyethylene (MDPE), metallocene-catalyzed medium density polyethylene (mMDPE), high density polyethylene (HDPE), a plastomer, an elastomer, or combinations thereof.

10. The method of claim 1, wherein the step (c) of identifying the two or more polymer components of the polymer sample accounts for the type of catalyst used for producing the two or more polymer components.

11. The method of claim 10, wherein the two or more polymer components comprise Ziegler-Natta-catalyzed linear low density polyethylene (ZN-LLDPE) and metallocene-catalyzed linear low density polyethylene (mLLDPE).

12. The method of claim 1, wherein the polymer resin is a polymer film, a multi-layer polymer film, a polymer blend, a unimodal polymer, a multimodal polymer, a bimodal polymer, a trimodal polymer, a terpolymer, or combinations thereof.

13. A method of producing a polymer resin comprising:
(a) providing a polymer sample of the polymer resin, wherein the polymer sample comprises two or more polymer components;
(b) subjecting at least a portion of the polymer sample to analytical temperature rising elution fractionation (aTREF) analysis to yield an aTREF elution trace;
(c) identifying the two or more polymer components of the polymer sample to yield two or more identified polymer components; wherein the identifying comprises comparing the aTREF elution trace with an identification library that comprises a plurality of known polymer aTREF elution traces, wherein each of the plurality of known polymer aTREF elution traces is correlated with a known polymer component, wherein the known polymer component is characterized by an identifying parameter, and wherein the identifying parameter is selected from the group consisting of density, short chain branching, crystallization temperature, melt index, high load melt index, molecular weight distribution, and combinations thereof;
(d) quantifying an amount of each of the two or more identified polymer components in the polymer sample to yield two or more quantified polymer components, wherein the quantifying comprises chemometric analysis of the aTREF elution trace; and
(e) producing the polymer resin by:
(i) responsive to step (c), selecting one or more monomers that can form the two or more identified polymer components; and polymerizing the one or more monomers to produce the polymer resin; wherein the polymerizing occurs under a plurality of polymerization conditions; and wherein each polymerization condition of the plurality of polymerization conditions is selected responsive to step (d) from the group consisting of monomer concentration, comonomer concentration, hydrogen to monomer ratio, temperature, catalyst concentration, cocatalyst concentration, pressure, residence time, reactor solids concentration, and combinations thereof;
(ii) responsive to step (c), selecting the two or more polymer components; and responsive to step (d), blending the two or more polymer components to produce the polymer resin; or
(iii) both (i) and (ii).

14. The method of claim 13 further comprising forming the polymer resin produced in step (e) into an article.

15. A system for analyzing a polyethylene resin comprising:
an analytical instrument comprising an analytical temperature rising elution fractionation (aTREF) column and an infrared (IR) detector; wherein the aTREF column is configured to receive a polyethylene sample solution, wherein the polyethylene sample solution comprises a polyethylene sample of the polyethylene resin and an aTREF solvent, wherein the polyethylene sample comprises two or more polyethylene components; wherein the aTREF column is configured to elute the two or more polyethylene components at different elution rates along the aTREF column to produce an aTREF eluent; and wherein the IR detector is configured to detect the two or more polyethylene components in the aTREF eluent and yield an aTREF elution trace; and
a computer system configured to receive the aTREF elution trace from the analytical instrument, wherein the computer system comprises at least one processor; wherein the at least one processor compares the aTREF elution trace with an identification library and identifies the two or more polyethylene components of the polyethylene sample to yield two or more identified polyethylene components; wherein the identification library comprises a plurality of known polyethylene aTREF elution traces, wherein each of the plurality of known polyethylene aTREF elution traces is correlated with a known polyethylene component, wherein the known polyethylene component is characterized by an identifying parameter, and wherein the identifying parameter is selected from the group consisting of density, short chain branching, crystallization temperature, melt index, high load melt index, molecular weight distribution, and combinations thereof; and wherein the at least one processor performs chemometric analysis of the aTREF elution trace to quantify an amount of each of the two or more identified polyethylene components in the polyethylene sample to yield two or more quantified polyethylene components.

16. The system of claim 15, wherein the analytical instrument comprises an aTREF instrument, a crystallization elution fractionation (CEF) instrument, a crystallization analysis fractionation (CRYSTAF)-aTREF instrument, an aTREF-gel permeation chromatography (GPC) instrument, or combinations thereof.

17. The system of claim 16, wherein the CEF instrument further comprises a capillary viscometer detector configured to provide data on composition-molar mass interdependence of the two or more polyethylene components.

18. The system of claim 15 further comprising:
a polymerization reactor, wherein the polymerization reactor is configured to polymerize ethylene to produce the polyethylene resin; wherein the reactor operates under a plurality of polymerization conditions comprising monomer concentration, comonomer concentration, hydrogen to monomer ratio, temperature, catalyst concentration, cocatalyst concentration, pressure, residence time, reactor solids concentration, or combinations thereof; and
a control system configured to receive the amount of each of the two or more identified polyethylene components in the polyethylene sample from the computer system, wherein the control system comprises at least one controller; and wherein the at least one controller adjusts at least one of the plurality of polymerization conditions.

19. The system of claim 18 further comprising a shaping system configured to receive the polyethylene resin from the polymerization reactor, wherein the shaping system is configured to form at least a portion of the polyethylene resin into a shaped article.

20. The system of claim 18, wherein the polymerization reactor is selected from the group consisting of a loop slurry reactor, a fluidized bed gas phase reactor, a solution reactor, a continuous stirred-tank reactor (CSTR), an autoclave, a tubular reactor, a multi-zone circulating reactor (MZCR), and combinations thereof.

\* \* \* \* \*